US012746334B2

(12) United States Patent
Sanchez et al.

(10) Patent No.: US 12,746,334 B2
(45) Date of Patent: Sep. 29, 2026

(54) DRUG DELIVERY DEVICE HAVING REMOVABLE CAP

(71) Applicant: AMGEN INC., Thousand Oaks, CA (US)

(72) Inventors: Steve Sanchez, Thousand Oaks, CA (US); Michael John McColligan, Thousand Oaks, CA (US); Austin Davis, Thousand Oaks, CA (US); Yangkun Song, Thousand Oaks, CA (US); Anders Grove Sund, Copenhagen (DK); Gregory Thomas Nowak, Somerville, MA (US)

(73) Assignee: AMGEN INC., Thousand Oaks, CA (US)

( * ) Notice: Subject to any disclaimer, the term of this patent is extended or adjusted under 35 U.S.C. 154(b) by 1048 days.

(21) Appl. No.: 17/690,032

(22) Filed: Mar. 9, 2022

(65) Prior Publication Data

US 2022/0288315 A1 Sep. 15, 2022

Related U.S. Application Data

(60) Provisional application No. 63/159,317, filed on Mar. 10, 2021.

(51) Int. Cl.
*A61M 5/20* (2006.01)
*A61J 1/20* (2006.01)
(Continued)

(52) U.S. Cl.
CPC .............. *A61M 5/20* (2013.01); *A61J 1/2096* (2013.01); *A61M 5/2033* (2013.01); *A61M 5/24* (2013.01);
(Continued)

(58) Field of Classification Search
CPC ................ A61M 5/20; A61M 5/31535; A61M 5/31565; A61M 5/3202; A61M 5/3204;
(Continued)

(56) References Cited

U.S. PATENT DOCUMENTS

| | | | |
|---|---|---|---|
| 758,567 | A | 4/1904 | Siebelist. |
| 3,316,909 | A | 5/1967 | Cowley |

(Continued)

FOREIGN PATENT DOCUMENTS

| | | | |
|---|---|---|---|
| CA | 3127415 | A1 | 9/2020 |
| CN | 101868270 | A | 10/2010 |

(Continued)

OTHER PUBLICATIONS

Office Action received in Eurasian Patent Application No. 202392532, dated Oct. 19, 2023.

(Continued)

*Primary Examiner* — Tasnim Mehjabin Ahmed

(57) ABSTRACT

A drug delivery device including a housing, a drug storage container, and a removable cap is provided. The removable cap may be configured to be removably coupled with the housing such that the removable cap has a storage position where the removable cap is coupled with the housing and at least partially covering an opening in the housing and a removed position where the removable cap is not coupled with the housing. The removable cap may include an outer portion, an inner portion, and a gap separating at least a portion of the inner portion and at least a portion of the outer portion such that the at least a portion of the outer portion is allowed to bend with respect to the at least a portion of the inner portion if the at least a portion of the outer portion is subjected to an external force. Additionally or alternatively, the removable cap may be configured such that an external force applied to the removable cap induces at least one (Continued)

bending moment in a proximal end and/or a distal end of the removable cap.

20 Claims, 12 Drawing Sheets

(51) Int. Cl.
*A61M 5/24* (2006.01)
*A61M 5/315* (2006.01)
*A61M 5/32* (2006.01)
*A61M 5/31* (2006.01)

(52) U.S. Cl.
CPC .... *A61M 5/31535* (2013.01); *A61M 5/31565* (2013.01); *A61M 5/3202* (2013.01); *A61M 5/3204* (2013.01); *A61M 2005/206* (2013.01); *A61M 2005/208* (2013.01); *A61M 2005/3104* (2013.01); *A61M 2005/3106* (2013.01)

(58) Field of Classification Search
CPC .............. A61M 5/24; A61M 2005/206; A61M 2005/208; A61M 2005/3104; A61M 2005/3106; A61M 2005/2013; A61M 2005/3247; A61M 2005/3267
See application file for complete search history.

(56) References Cited

U.S. PATENT DOCUMENTS

| | | | |
|---|---|---|---|
| D321,472 | S | 11/1991 | Evans et al. |
| 5,098,400 | A | 3/1992 | Crouse et al. |
| 5,562,637 | A | 10/1996 | Utterberg |
| 5,569,192 | A | 10/1996 | van der Wal |
| 5,964,731 | A | 10/1999 | Kovelman |
| D443,641 | S | 6/2001 | Mader |
| 6,447,480 | B1 | 9/2002 | Brunel |
| 6,454,746 | B1 | 9/2002 | Bydlon et al. |
| 6,575,939 | B1 | 6/2003 | Brunel |
| 6,585,702 | B1 | 7/2003 | Brunel |
| D497,806 | S | 11/2004 | Nichols et al. |
| D509,296 | S | 9/2005 | Minshull et al. |
| D545,895 | S | 7/2007 | Okutani |
| 7,247,153 | B2 | 7/2007 | Guala |
| 7,370,759 | B2 | 5/2008 | Hommann |
| 7,397,730 | B2 | 7/2008 | Skyggebjerg et al. |
| 7,597,685 | B2 | 10/2009 | Olson |
| D605,006 | S | 12/2009 | Shiao |
| D612,486 | S | 3/2010 | Van der Stappen |
| D616,089 | S | 5/2010 | Van der Stappen |
| D619,244 | S | 7/2010 | Van der Stappen |
| D620,106 | S | 7/2010 | Van der Stappen |
| D621,929 | S | 8/2010 | Van der Stappen |
| D622,374 | S | 8/2010 | Julian et al. |
| 7,771,397 | B1 | 8/2010 | Olson |
| D623,738 | S | 9/2010 | Van der Stappen |
| 7,794,432 | B2 | 9/2010 | Young et al. |
| 7,806,861 | B2 | 10/2010 | Witowski |
| D626,994 | S | 11/2010 | Gerules |
| D627,061 | S | 11/2010 | Van der Stappen |
| D628,690 | S | 12/2010 | Galbraith |
| D629,509 | S | 12/2010 | Julian et al. |
| D640,786 | S | 6/2011 | Sato et al. |
| 7,988,675 | B2 | 8/2011 | Gillespie, III et al. |
| 8,062,255 | B2 | 11/2011 | Brunnberg et al. |
| D660,958 | S | 5/2012 | Mcloughlin et al. |
| 8,298,194 | B2 | 10/2012 | Schmidt |
| D671,638 | S | 11/2012 | Young et al. |
| 8,313,470 | B2 | 11/2012 | Abry |
| 8,357,125 | B2 | 1/2013 | Grunhut et al. |
| 8,361,025 | B2 | 1/2013 | Lawlis et al. |
| 8,372,035 | B2 | 2/2013 | Matusch |
| D678,514 | S | 3/2013 | Foley et al. |
| D683,016 | S | 5/2013 | Mirza et al. |
| 8,529,518 | B2 | 9/2013 | Larsen et al. |
| 8,568,359 | B2 | 10/2013 | Carrel et al. |
| 8,568,364 | B2 | 10/2013 | Plumptre |
| D692,998 | S | 11/2013 | Broberg et al. |
| D696,397 | S | 12/2013 | Guarraia et al. |
| D696,770 | S | 12/2013 | Schneider et al. |
| D696,772 | S | 12/2013 | Schneider et al. |
| D696,773 | S | 12/2013 | Schneider et al. |
| D696,774 | S | 12/2013 | Guarraia et al. |
| D696,775 | S | 12/2013 | Guarraia et al. |
| 8,608,709 | B2 | 12/2013 | Moeller et al. |
| D697,205 | S | 1/2014 | Schneider et al. |
| 8,647,299 | B2 | 2/2014 | Stamp |
| 8,696,618 | B2 | 4/2014 | Kramer et al. |
| 8,740,871 | B2 | 6/2014 | Lawlis et al. |
| D708,317 | S | 7/2014 | Schneider et al. |
| 8,814,828 | B2 | 8/2014 | Llewellyn-Hyde et al. |
| 8,817,258 | B2 | 8/2014 | Whalley et al. |
| D714,932 | S | 10/2014 | Hall et al. |
| D715,422 | S | 10/2014 | Hall et al. |
| D717,428 | S | 11/2014 | Sendatzki et al. |
| 8,882,722 | B2 | 11/2014 | Bode et al. |
| D721,802 | S | 1/2015 | Ohashi |
| D722,158 | S | 2/2015 | Magome et al. |
| D722,256 | S | 2/2015 | Kita |
| 8,945,065 | B2 | 2/2015 | Torris et al. |
| 8,945,067 | B2 | 2/2015 | Mcloughlin et al. |
| 8,992,484 | B2 | 3/2015 | Radmer et al. |
| D726,902 | S | 4/2015 | Mcloughlin et al. |
| D728,782 | S | 5/2015 | Dubuc et al. |
| 9,022,982 | B2 | 5/2015 | Karlsson et al. |
| 9,033,932 | B2 | 5/2015 | Holmqvist |
| D732,161 | S | 6/2015 | Ohashi |
| D732,661 | S | 6/2015 | Dubuc et al. |
| D733,869 | S | 7/2015 | Ratjen |
| 9,072,833 | B2 | 7/2015 | Jennings et al. |
| 9,078,973 | B2 | 7/2015 | Harms et al. |
| D735,848 | S | 8/2015 | Dubuc et al. |
| 9,114,212 | B2 | 8/2015 | Enggaard et al. |
| D737,639 | S | 9/2015 | Masalin et al. |
| D739,011 | S | 9/2015 | Morrison et al. |
| D739,932 | S | 9/2015 | Ratjen et al. |
| 9,174,000 | B2 | 11/2015 | Bode |
| 9,233,212 | B2 | 1/2016 | Holmqvist |
| 9,238,111 | B2 | 1/2016 | Marshall et al. |
| 9,242,050 | B2 | 1/2016 | Abry |
| 9,272,094 | B2 | 3/2016 | Boyd et al. |
| 9,295,784 | B2 | 3/2016 | Eggert et al. |
| 9,302,053 | B2 | 4/2016 | Holmqvist |
| D755,956 | S | 5/2016 | Mcloughlin et al. |
| D757,255 | S | 5/2016 | Wohlfahrt et al. |
| 9,333,305 | B2 | 5/2016 | Mcloughlin et al. |
| 9,339,610 | B2 | 5/2016 | Julian et al. |
| D758,566 | S | 6/2016 | Chen |
| D758,567 | S | 6/2016 | Wohlfahrt et al. |
| D758,568 | S | 6/2016 | Wohlfahrt et al. |
| D758,569 | S | 6/2016 | Wohlfahrt et al. |
| D758,570 | S | 6/2016 | Wohlfahrt et al. |
| D758,571 | S | 6/2016 | Geert-Jensen et al. |
| D759,813 | S | 6/2016 | Newman et al. |
| D759,814 | S | 6/2016 | Newman et al. |
| D765,239 | S | 8/2016 | Hauck et al. |
| D765,240 | S | 8/2016 | Hauck et al. |
| 9,421,336 | B2 | 8/2016 | Ekman et al. |
| D766,425 | S | 9/2016 | Hauck et al. |
| D767,119 | S | 9/2016 | Hauck et al. |
| D770,610 | S | 11/2016 | Saussaye et al. |
| D773,648 | S | 12/2016 | Wohlfahrt et al. |
| D773,650 | S | 12/2016 | Fourt et al. |
| D774,639 | S | 12/2016 | Saussaye et al. |
| D774,641 | S | 12/2016 | Miggels et al. |
| D775,279 | S | 12/2016 | Shen |
| D780,909 | S | 3/2017 | Burkett et al. |
| D783,816 | S | 4/2017 | Wohlfahrt et al. |
| 9,623,199 | B2 | 4/2017 | Richter et al. |
| 9,656,027 | B2 | 5/2017 | Quinn |
| D788,909 | S | 6/2017 | Ratjen |
| D789,519 | S | 6/2017 | Ratjen et al. |
| D790,686 | S | 6/2017 | Cox et al. |

(56) References Cited

U.S. PATENT DOCUMENTS

| | | | |
|---|---|---|---|
| D793,547 | S | 8/2017 | Burkett et al. |
| D794,178 | S | 8/2017 | Daniel et al. |
| D794,777 | S | 8/2017 | Daniel et al. |
| D794,778 | S | 8/2017 | Daniel et al. |
| D799,026 | S | 10/2017 | Jones et al. |
| D802,748 | S | 11/2017 | Mills et al. |
| D802,751 | S | 11/2017 | Ratjen et al. |
| D809,137 | S | 1/2018 | Ratjen |
| D810,280 | S | 2/2018 | Tharp et al. |
| D810,282 | S | 2/2018 | Ratjen |
| 9,895,493 | B2 | 2/2018 | Burnell et al. |
| D812,746 | S | 3/2018 | Umemura |
| D813,379 | S | 3/2018 | Mills et al. |
| D814,022 | S | 3/2018 | Boyaval et al. |
| RE46,789 | E | 4/2018 | Olson |
| D815,732 | S | 4/2018 | Mills et al. |
| D816,212 | S | 4/2018 | Daniel et al. |
| D819,198 | S | 5/2018 | Boyaval et al. |
| D819,200 | S | 5/2018 | Stonecipher et al. |
| D819,804 | S | 6/2018 | Knight et al. |
| 9,987,436 | B2 | 6/2018 | Giambattista et al. |
| D822,198 | S | 7/2018 | Stonecipher et al. |
| D822,199 | S | 7/2018 | Clawson et al. |
| D823,459 | S | 7/2018 | Bendek et al. |
| D827,127 | S | 8/2018 | Donnelly |
| D827,128 | S | 8/2018 | Boyaval et al. |
| D830,539 | S | 10/2018 | Boyaval et al. |
| D831,822 | S | 10/2018 | Guillermo et al. |
| 10,159,795 | B2 | 12/2018 | Cave |
| 10,265,476 | B2 | 4/2019 | Laiosa et al. |
| D851,754 | S | 6/2019 | Boyaval et al. |
| 10,335,553 | B2 | 7/2019 | Bendek |
| D857,192 | S | 8/2019 | Burkett et al. |
| D861,859 | S | 10/2019 | Rapp et al. |
| D864,378 | S | 10/2019 | Tafazoli et al. |
| D866,751 | S | 11/2019 | Rogge et al. |
| D866,752 | S | 11/2019 | Rogge et al. |
| D866,757 | S | 11/2019 | Diluzio et al. |
| D867,588 | S | 11/2019 | Rogge et al. |
| D868,245 | S | 11/2019 | Holmqvist et al. |
| D868,961 | S | 12/2019 | Stewart et al. |
| D870,270 | S | 12/2019 | Burkett et al. |
| 10,512,725 | B1 | 12/2019 | Bauss et al. |
| D878,560 | S | 3/2020 | Boyaval et al. |
| D878,563 | S | 3/2020 | Clawson et al. |
| D878,564 | S | 3/2020 | Clawson et al. |
| D878,566 | S | 3/2020 | Jansen |
| D882,071 | S | 4/2020 | Stonecipher et al. |
| RE48,006 | E | 5/2020 | Fourt et al. |
| D883,475 | S | 5/2020 | Boyaval et al. |
| D884,161 | S | 5/2020 | Stewart et al. |
| D886,281 | S | 6/2020 | Boyaval et al. |
| D886,282 | S | 6/2020 | Stonecipher et al. |
| D892,311 | S | 8/2020 | Nicholas et al. |
| D892,312 | S | 8/2020 | Nicholas et al. |
| D893,710 | S | 8/2020 | Neby |
| 10,780,256 | B2 | 9/2020 | Cordoba et al. |
| D898,189 | S | 10/2020 | Boyaval et al. |
| D898,900 | S | 10/2020 | Atterbury et al. |
| D917,064 | S | 4/2021 | Ribeiro et al. |
| D922,566 | S | 6/2021 | Ono |
| D922,567 | S | 6/2021 | Boyaval et al. |
| D931,443 | S | 9/2021 | Bainton et al. |
| D936,824 | S | 11/2021 | Donnelly |
| D956,212 | S | 6/2022 | Petersen et al. |
| D958,329 | S | 7/2022 | Bourelle et al. |
| D962,423 | S | 8/2022 | Melander et al. |
| D973,866 | S | 12/2022 | Bourelle et al. |
| D974,547 | S | 1/2023 | O'Malley et al. |
| 2004/0068283 | A1 | 4/2004 | Fukuzawa et al. |
| 2005/0148933 | A1 | 7/2005 | Raven et al. |
| 2006/0100655 | A1 | 5/2006 | Leong et al. |
| 2008/0269682 | A1 | 10/2008 | Kavazov et al. |
| 2008/0269692 | A1 | 10/2008 | James et al. |
| 2009/0054849 | A1 | 2/2009 | Burnell et al. |
| 2009/0234297 | A1 | 9/2009 | Jennings |
| 2010/0152659 | A1 | 6/2010 | Streit et al. |
| 2010/0268169 | A1* | 10/2010 | Llewellyn-Hyde .......................... A61M 5/5086 604/192 |
| 2011/0098656 | A1 | 4/2011 | Burnell et al. |
| 2012/0089098 | A1 | 4/2012 | Boyd et al. |
| 2012/0123347 | A1 | 5/2012 | Boyd et al. |
| 2012/0123350 | A1 | 5/2012 | Giambattista et al. |
| 2012/0197208 | A1 | 8/2012 | Bruggemann et al. |
| 2012/0232474 | A1 | 9/2012 | Nielsen et al. |
| 2013/0035645 | A1 | 2/2013 | Bicknell et al. |
| 2013/0060231 | A1 | 3/2013 | Adlon et al. |
| 2013/0150802 | A1 | 6/2013 | Claughton |
| 2013/0211330 | A1 | 8/2013 | Pedersen et al. |
| 2013/0211340 | A1 | 8/2013 | Helmer |
| 2013/0274671 | A1 | 10/2013 | Jennings et al. |
| 2013/0281933 | A1 | 10/2013 | Cowe et al. |
| 2013/0310746 | A1 | 11/2013 | Robert |
| 2013/0331796 | A1 | 12/2013 | Wozencroft |
| 2014/0012205 | A1 | 1/2014 | Jugl et al. |
| 2014/0094743 | A1 | 4/2014 | Bengtsson |
| 2014/0101912 | A1 | 4/2014 | Abry |
| 2014/0207073 | A1 | 7/2014 | Shang et al. |
| 2014/0213985 | A1 | 7/2014 | Teucher et al. |
| 2014/0221916 | A1 | 8/2014 | Kramer et al. |
| 2014/0221936 | A1 | 8/2014 | Edhouse et al. |
| 2014/0228769 | A1 | 8/2014 | Karlsson et al. |
| 2014/0243750 | A1 | 8/2014 | Larsen et al. |
| 2014/0243753 | A1 | 8/2014 | Boström |
| 2014/0323976 | A1 | 10/2014 | Jugl et al. |
| 2014/0330216 | A1 | 11/2014 | Weaver et al. |
| 2014/0336588 | A1 | 11/2014 | Mcloughlin et al. |
| 2014/0343503 | A1* | 11/2014 | Holmqvist .......... A61M 5/3204 81/3.4 |
| 2014/0343507 | A1 | 11/2014 | Karlsson et al. |
| 2014/0364812 | A1 | 12/2014 | Lumme et al. |
| 2014/0371684 | A1 | 12/2014 | Holmqvist |
| 2015/0051553 | A1 | 2/2015 | Björk et al. |
| 2015/0133875 | A1 | 5/2015 | Oakland |
| 2015/0174325 | A1 | 6/2015 | Young et al. |
| 2015/0190577 | A1 | 7/2015 | Shaanan et al. |
| 2015/0202368 | A1 | 7/2015 | Carrel et al. |
| 2015/0290396 | A1 | 10/2015 | Nagar et al. |
| 2015/0335829 | A1 | 11/2015 | Giambattista et al. |
| 2015/0367081 | A1 | 12/2015 | Rosenthal |
| 2016/0082198 | A1 | 3/2016 | Holmqvist |
| 2016/0106929 | A1 | 4/2016 | Fournier et al. |
| 2016/0144132 | A1 | 5/2016 | Scanlon |
| 2016/0151586 | A1 | 6/2016 | Kemp |
| 2016/0193413 | A1 | 7/2016 | Gabrielsson |
| 2016/0199589 | A1 | 7/2016 | Plumptre |
| 2016/0220763 | A1 | 8/2016 | Teucher et al. |
| 2016/0250421 | A1 | 9/2016 | Fincham et al. |
| 2016/0263325 | A1 | 9/2016 | Huthmacher et al. |
| 2016/0303327 | A1* | 10/2016 | Moren ................ A61M 5/2033 |
| 2017/0128668 | A1 | 5/2017 | Miller et al. |
| 2017/0182242 | A1 | 6/2017 | Galitz et al. |
| 2018/0043101 | A1 | 2/2018 | Weaver et al. |
| 2018/0104413 | A1 | 4/2018 | Mcloughlin et al. |
| 2019/0247589 | A1 | 8/2019 | Holmqvist et al. |
| 2019/0266921 | A1 | 8/2019 | Chang |
| 2019/0298924 | A1 | 10/2019 | Gibson et al. |
| 2019/0328485 | A1 | 10/2019 | Bauss et al. |
| 2020/0179612 | A1 | 6/2020 | Wei |
| 2020/0188607 | A1 | 6/2020 | Knight et al. |
| 2020/0258425 | A1 | 8/2020 | Foley et al. |
| 2020/0289753 | A1 | 9/2020 | Andréet al. |
| 2021/0093789 | A1 | 4/2021 | Plambech et al. |
| 2021/0093796 | A1 | 4/2021 | Finkelstein et al. |
| 2021/0093797 | A1 | 4/2021 | Finkelstein et al. |
| 2021/0093799 | A1 | 4/2021 | Perot et al. |
| 2021/0121633 | A1 | 4/2021 | Finkelstein et al. |
| 2022/0288324 | A1 | 9/2022 | Davis et al. |

FOREIGN PATENT DOCUMENTS

| | | | |
|---|---|---|---|
| CN | 302858428 | S | 6/2014 |
| CN | 304223460 | S | 7/2017 |

(56) References Cited

FOREIGN PATENT DOCUMENTS

| | | | |
|---|---|---|---|
| CN | 307287422 | S | 4/2022 |
| EM | 003372911-0002 | | 9/2016 |
| EM | 008038723-0005 | | 7/2020 |
| EP | 0896827 | A1 | 2/1999 |
| EP | 1053037 | A1 | 11/2000 |
| EP | 1755706 | A1 | 2/2007 |
| EP | 2253348 | A1 | 11/2010 |
| EP | 2255842 | A1 | 12/2010 |
| EP | 2298390 | A1 | 3/2011 |
| EP | 2361648 | A1 | 8/2011 |
| EP | 2555820 | A2 | 2/2013 |
| EP | 2729203 | A1 | 5/2014 |
| EP | 2788048 | A1 | 10/2014 |
| EP | 2878321 | A1 | 6/2015 |
| EP | 2902063 | A1 | 8/2015 |
| EP | 3038682 | A1 | 7/2016 |
| EP | 3184138 | A1 | 6/2017 |
| GB | 9003372911-0001 | | 9/2016 |
| GB | 9008041362-0012 | | 7/2020 |
| GB | 6133321 | | 4/2021 |
| GB | 6133347 | | 4/2021 |
| GB | 6133354 | | 4/2021 |
| GB | 6133358 | | 4/2021 |
| IL | 67773 | A | 2/1985 |
| JP | 2010-540055 | A | 12/2010 |
| JP | 1607619 | S | 6/2018 |
| JP | 1634556 | S | 6/2019 |
| JP | 2020-510490 | A | 4/2020 |
| JP | 2020-534959 | A | 12/2020 |
| JP | 1691711 | S | 8/2021 |
| RU | 100256 | U1 | 12/2010 |
| RU | 100299 | U1 | 12/2010 |
| TW | D179360 | | 11/2016 |
| TW | D179362 | | 11/2016 |
| TW | 201731548 | A | 9/2017 |
| WO | 99/39759 | A1 | 8/1999 |
| WO | 02/87670 | A1 | 11/2002 |
| WO | 2005/115508 | A1 | 12/2005 |
| WO | 2010/142812 | A1 | 12/2010 |
| WO | 2011/126439 | A1 | 10/2011 |
| WO | 2012/003516 | A2 | 1/2012 |
| WO | 2012/065965 | A1 | 5/2012 |
| WO | 2013/006119 | A1 | 1/2013 |
| WO | 2013/085454 | A1 | 6/2013 |
| WO | 2013/139894 | A1 | 9/2013 |
| WO | 2014/096957 | A2 | 6/2014 |
| WO | 2014/118105 | A1 | 8/2014 |
| WO | 2015/001819 | A1 | 1/2015 |
| WO | 2015/028488 | A1 | 3/2015 |
| WO | 2015/085068 | A1 | 6/2015 |
| WO | 2015/110533 | A2 | 7/2015 |
| WO | 2016/055334 | A1 | 4/2016 |
| WO | 2016/062807 | A1 | 4/2016 |
| WO | 2016/102299 | A1 | 6/2016 |
| WO | 2016/198387 | A1 | 12/2016 |
| WO | 2018/111796 | A1 | 6/2018 |
| WO | 2018/202458 | A1 | 11/2018 |
| WO | 2021/030066 | A1 | 2/2021 |

OTHER PUBLICATIONS

Aimovig, Amgen, [Postdate unknown], [Site seen Sep. 6, 2022], Seen at URL: https://www.amgeninjectiondemos.com/Aimovig (Year: 2022).

Parental Drug Association, "Trends in the Self-injection Device Market & next Generation Platform Technologies," [postdate 2018], [Site seen Sep. 6, 2022], Seen at URL: https://pda-asiapacific.glueup.com/resources/protected/organization/1176/event/26285/93bd1ce6-33aa-48c1-b0b7-9833dd5155bc.pdf (Year: 2022).

U.S. Appl. No. 29/773,601, Non-Final Office Action, mailed Sep. 14, 2022.

U.S. Appl. No. 16/832,987, Non-Final Office Action, mailed Sep. 29, 2022.

[30 Years in the Making—An Inside Perspective on the Emergence of Autoin Jectors], available on ON drug Delivery Magazine, Issue 101 (Oct. 2019), pp. 20-23, by McGowan M, published Oct. 2, 2019 [online], [site visited Dec. 7, 2021], Internet URL: <https://www.ondrugdelivery.com/wp-content/uploads/2019/09/101_2019_SHL_article.pdf> (Year: 2019).

Auto Injectors, Pen Injectors and Inhaler Systems, Pharmaceutical Technology, [postdate: unknown], [Site seen May 3, 2022], Seen at URL: https://www.pharmaceutical-technology.com/contractors/drug_delivery/shl-group/ (Year: 2022).

BD Vystra Disposable Pen, BD.com, [Postdate: Jan. 9, 2019], [Site seen May 3, 2022], Seen at URL: https://drugdeliverysystems.bd.com/products/self-injection-systems/vystra-disposable-pen (Year: 2019).

Industrial Design DM/092744, Millennium Pharmaceuticals, Inc., Registration date Sep. 6, 2016.

International Application No. PCT/US22/19414, International Search Report and Written Opinion, mailed Jul. 1, 2022.

International Application No. PCT/US22/19418, International Search Report and Written Opinion, mailed Jul. 13, 2022.

Internet publication https://www.youtube.com/watch?v=VbGb5lt9n80, dated Sep. 30, 2014.

Mcgowan, 30 Years in the Making—An Inside Perspective on the Emergency of Autoinjectors, ONdrugDelivery Magazine, Issue 101, pp. 20-23 (Oct. 2019).

Office Action and Search Report for Taiwan application No. 1066305338, dated Mar. 26, 2018.

Office Action, Israel Design Office, Application No. 60912, Mar. 4, 2018.

Roy et al., Autoinjector—A smart device for emergency cum personal therapy, Saudi Pharmaceutical Journal, 29(10):1205-1215 (2021).

U.S. Appl. No. 29/644,412, Notice of Allowance, mailed Jan. 8, 2020.

U.S. Appl. No. 29/645,820, Notice of Allowance, mailed Mar. 5, 2020.

U.S. Appl. No. 29/654,799, Notice of Allowance, mailed Apr. 1, 2020.

U.S. Appl. No. 29/654,799, Notice of Allowance, mailed Jan. 2, 2020.

U.S. Appl. No. 29/661,300, Notice of Allowance, mailed Jan. 8, 2020.

U.S. Appl. No. 29/723,028, Notice of Allowance, mailed Jun. 1, 2020.

U.S. Appl. No. 29/723,028, Requirement for Restriction, mailed Apr. 7, 2020.

U.S. Appl. No. 29/726,050, Ex Parte Quayle Action, mailed Jan. 7, 2022.

U.S. Appl. No. 29/726,050, Notice of Allowance, mailed Mar. 23, 2022.

U.S. Appl. No. 29/773,601, Requirement for Restriction/Election, mailed Jun. 22, 2022.

U.S. Appl. No. 29/773,604, Requirement for Restriction/Election, mailed Jun. 22, 2022.

U.S. Appl. No. 29/776,495, Requirement for Restriction/Election, mailed Jun. 22, 2022.

Notice of Allowance received for U.S. Appl. No. 29/757,411, mailed on Sep. 16, 2022, 8 pages.

Requirement for Restriction/Election received for received for U.S. Appl. No. 29/757,411, mailed on Jun. 22, 2022, 6 pages.

U.S. Appl. No. 12/597,230, Notice of Allowance, mailed Jan. 11, 2023.

U.S. Appl. No. 29/757,416, Notice of Allowance, mailed Sep. 16, 2022.

U.S. Appl. No. 29/757,416, Requirement for Restriction/Election, mailed Jun. 22, 2022.

U.S. Appl. No. 29/773,604, Non-Final Office Action, mailed Sep. 27, 2022.

U.S. Appl. No. 29/776,495, Non-Final Office Action, mailed Sep. 27, 2022.

U.S. Appl. No. 29/776,495, Notice of Allowance, mailed Jan. 20, 2023.

U.S. Appl. No. 29/783,469, Requirement for Restriction/Election, mailed Dec. 20, 2022.

(56) References Cited

OTHER PUBLICATIONS

First Examination Report received in counterpart Saudi Arabia Patent Application No. 523450640, dated Oct. 27, 2024.
"Innovating in the viscosity design space with a new 2.25 mL autoinjector platform", BD InteviaTM, downloaded from the Internet at: <https://www.cphi-online.com/innovating-in-the-viscosity-design-space-with-a-news112108.html> (Year: 2021).
Amneal Pharamceuticals, Epinephrine Auto-Injector, downloaded from the Internet at: <https://www.safcodental.com/catalog/pharmaceuticals-and-otc/pain-relievers-and-antibiotics/epinephrine-auto-injector> (Year: 2023).
Owen Mumford Pharmaceutical Services, Auto-injectors for intramuscular and subcutaneous administration, [Post date unknown] downloaded from the Internet at: <https://www.owenmumford.com/en/drug-delivery/auto-injectors> (Year: 2023).
PiccoJect self injector, Haselmeier, downloaded from the Internet at: <https://globaldesignnews.com/this-compact-user-focused-auto-injector-platform-innovates-with-improved-features-that-address-key-challenges-making%E2%80%A6> (Year: 2023).
SHL Group, Auto Injectors & Pen Injectors: A user-centric design approach, downloaded from the Internet at: <https://www.ondrugdelivery.com/wp-content/uploads/2017/05/SHL-HR.pdf> (2015).
U.S. Appl. No. 29/773,604, Notice of Allowance, mailed Feb. 6, 2023.

* cited by examiner

DRUG DELIVERY DEVICE HAVING REMOVABLE CAP

CROSS-REFERENCE TO RELATED APPLICATION

Priority is claimed to U.S. Provisional Patent Application No. 63/159,317, filed Mar. 10, 2021, the entire contents of which are hereby expressly incorporated by reference herein.

FIELD OF DISCLOSURE

The present disclosure generally relates to drug delivery devices and, more particularly, devices for automatically injecting a drug into a patient.

BACKGROUND

A general aversion to exposed needles, as well as health and safety issues, have led to the development of drug delivery devices which conceal a needle or other insertion member prior to use and which automate various aspects of an injection process. Such devices offer a variety of benefits as compared with traditional forms of drug delivery including, for example, delivery via a conventional syringe.

A drug delivery device may incorporate various mechanisms to implement various automated or semi-automated features. Such features may include automatically covering a needle in a pre-delivery and/or post-delivery state, automatically inserting a needle and/or a cannula into a user, automatically activating a drive mechanism, automatically indicating to the user that drug delivery is complete, locking a guard in a needle covering position after drug delivery is complete, among other features. Certain such features are activated by the application of an external force, for example, by a user. Such features may be prone to premature or inadvertent activation in cases where the drug delivery device subjected to a sudden unintended force or motion during manufacture, transport, storage, and/or other handling of the device.

For example, a drug delivery device may experience a substantial impulse force if it is dropped from a height and strikes a stationary surface such as the ground. The impulse force has the potential to prematurely activate the automated or semi-automated features and/or cause structural damage to the drug delivery device. The likelihood of such problems is increased if the drug delivery device has recently been removed from cold storage, which is required for drug delivery devices containing certain drugs. In a cold state, various components of the drug delivery device may be relatively brittle and thus vulnerable to fracture or damage as the result of a sudden impact.

The present disclosure sets forth drug delivery devices embodying advantageous alternatives to existing drug delivery devices, and removable cap features, and that may address one or more of the challenges or needs mentioned herein.

SUMMARY

One aspect of the present disclosure provides a drug delivery device including a housing, a drug storage container, and a removable cap. The housing may have an opening. The drug storage container may include a delivery member having an insertion end configured to extend at least partially through the opening during a delivery state. The removable cap may include an outer portion and an inner portion. The outer portion may be configured to be removably coupled with the housing such that the removable cap has a storage position where the removable cap is coupled with the housing and at least partially covering the opening and a removed position where the removable cap is not coupled with the housing. A gap may separate at least a portion of the inner portion and at least a portion of the outer portion such that the at least a portion of the outer portion is allowed to bend with respect to the at least a portion of the inner portion if the at least a portion of the outer portion is subjected to an external force.

The outer portion may entirely or partially surround the inner portion. The removable cap may have a first axial opening configured to receive the housing and a second axial opening. The outer portion may partially or entirely surrounds the first axial opening and/or the second axial opening. The gap may be a radial gap.

The removable cap may include one or more support members disposed between the inner portion and the outer portion. The support member(s) may be coupled with the inner portion and/or the outer portion. If multiple support members are included, they may be arranged at a respective circumferential positions around the inner portion.

One or more side openings may be formed in the outer portion and may communicate with the gap. The side opening(s) may be partially or entirely formed in a distally directed end surface of the outer portion. The side opening (s) may be proximal to a distally directed end surface of the outer portion. If multiple side openings are included, the may be arranged at respective circumferential positions around the outer portion.

The drug delivery device may include a removable sterile barrier configured to be removably coupled with the drug storage container such that the removable sterile barrier has a storage position where the removable sterile barrier is coupled with the drug storage container and at least partially covering the insertion end of the delivery member and a removed position where the removable sterile barrier is not coupled with the drug storage container. The removable sterile barrier may be a rigid needle shield (RNS). The inner portion of the removable cap may be coupled with and/or define a gripper configured to engage the removable sterile barrier such that when the removable cap is removed from the housing the gripper removes the removable sterile barrier from the drug storage container to uncover the insertion end of the delivery member. The gripper may be configured to rotate with respect to the removable sterile barrier during, for example, rotational movement of the removable cap with respect to the housing.

The removable cap may be configured such that the external force induces at least one bending moment in at least one of a proximal end of the removable cap and a distal end of the removable cap.

Another aspect of the present disclosure provides a drug delivery device including a housing, a drug storage container, and a removable cap. The drug storage container may include a delivery member having an insertion end configured to extend at least partially through the opening during a delivery state. The removable cap may include a distal end and a proximal end. The proximal end may be configured to be removably coupled with the housing such that the removable cap has a storage position where the removable cap is coupled with the housing and at least partially covering the opening and a removed position where the removable cap is not coupled with the housing. The removable cap may be configured such that an external force applied to the removable cap induces at least one bending moment in at least one of the proximal end of the removable cap and the distal end of the removable cap.

The at least one bending moment may include multiple, distinct bending moments, including, for example, a first bending moment, a second bending moment, and/or a third bending moment. The first bending moment may be partially or entirely in the proximal end of the removable cap. The second bending moment may be partially or entirely in the distal end of the removable cap. The third bending moment may be partially or entirely in a gripper included as part of or coupled with the removable cap.

The first bending moment may be associated with a portion of or the entirety of the proximal end of the removable cap bending partially or entirely around a first bending axis. The second bending moment may be associated with a portion of or the entirety of the distal end of the removable cap bending partially or entirely around a second bending axis. The third bending moment may be associated with a portion of or the entirety of the gripper bending partially or entirely around a third bending axis. The first bending axis, the second bending axis, and/or the third bending axis may be generally perpendicular or otherwise non-parallel to a longitudinal axis of the housing and/or removable cap.

The drug delivery device may include a removable sterile barrier configured to be removably coupled with the drug storage container such that the removable sterile barrier has a storage position where the removable sterile barrier is coupled with the drug storage container and at least partially covering the insertion end of the delivery member and a removed position where the removable sterile barrier is not coupled with the drug storage container. The removable sterile barrier may be a rigid needle shield (RNS). The gripper may be configured to engage the removable sterile barrier such that when the removable cap is removed from the housing the gripper removes the removable sterile barrier from the drug storage container to uncover the insertion end of the delivery member. The gripper may be configured to rotate with respect to the removable sterile barrier during, for example, rotational movement of the removable cap with respect to the housing.

The removable cap may include an outer portion and an inner portion. A gap may separate at least a portion of the inner portion and at least a portion of the outer portion such that the at least a portion of the outer portion is allowed to bend with respect to the at least a portion of the inner portion if the at least a portion of the outer portion is subjected to the external force.

The external force may be applied to the removable cap in a direction that is generally parallel to a longitudinal axis of the housing and/or removable cap.

The removable cap is made partially or entirely of a resilient material. The resilient material may include a polypropylene random copolymer.

The entirety of or a portion of the distal end of the removable cap may have a non-circular cross-section in a plane perpendicular to a longitudinal axis of the removable cap. The non-circular cross-section may be generally square-shaped. The entirety of or a portion of the proximal end of the removable cap may have a circular cross-section in a plane perpendicular to a longitudinal axis of the removable cap.

The housing may include a housing camming feature and the removable cap comprises a cap camming feature. The cap camming feature and the housing camming feature may be configured to translate rotational motion into axial motion such that, upon rotational movement of the removable cap with respect to the housing, the cap camming feature and/or the housing camming feature urge the removable cap along a longitudinal axis of the housing and/or removable cap.

The drug delivery device may include a plunger, a plunger biasing member, and/or a guard. The plunger may be moveable in a distal direction with respect to the drug storage container to expel a drug from the drug storage container through the delivery member during the delivery state. The plunger biasing member may be configured to urge the plunger in the distal direction. The guard may be operably coupled with the plunger biasing member such that a relative movement between the guard and the housing along the longitudinal axis of the housing and/or removable cap permits release of the plunger biasing member.

The drug delivery device may be an autoinjector but is not limited to being an autoinjector.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to drug delivery devices operable by a user for administering a drug, or in the case where a patient is the user, self-administering a drug. The drug delivery device may include a housing having an opening and a drug storage container including a delivery member having an insertion end configured to extend at least partially through the opening during a delivery state. The drug delivery device may also include a removable cap configured to be removably coupled with the housing such that the removable cap has a storage position where the removable cap is coupled with the housing and at least partially covering the opening and a removed position where the removable cap is not coupled with the housing. Generally, the removable cap may be configured with one or more shock absorbing features to mitigate or eliminate the undesirable effects of a sudden externally applied force, including, for example, an impulse force applied to the removable cap as a result of dropping the drug delivery device from a height onto a stationary surface such as the ground, a floor, a tabletop, a countertop, etc. The presently disclosed shock absorbing features may allow the removable cap or certain portion(s) thereof to bend (e.g., elastically bend) to diminish or dampen at least of some of the mechanical effects of the externally applied force including, for example, reducing an acceleration and/or deceleration caused by the externally applied force. Accordingly, the shock absorbing features may prevent or inhibit the activation of one or more automated or semi-automated features included in the drug delivery device including, for example, a drive mechanism for expelling a drug, a guard locking mechanism, among others. In addition, the presently disclosed shock absorbing features may prevent or inhibit damage to the drug delivery device, including the removable cap, that may otherwise result from the externally applied force. For example, the shock absorbing features may diminish the likelihood of fractures or cracks forming in the removable cap and/or other portions of the drug delivery device if a user accidentally drops the drug delivery device after removing it from cold storage. These and other advantages will be apparent to one of ordinary skill in the art reviewing the present disclosure.

Figure 1:
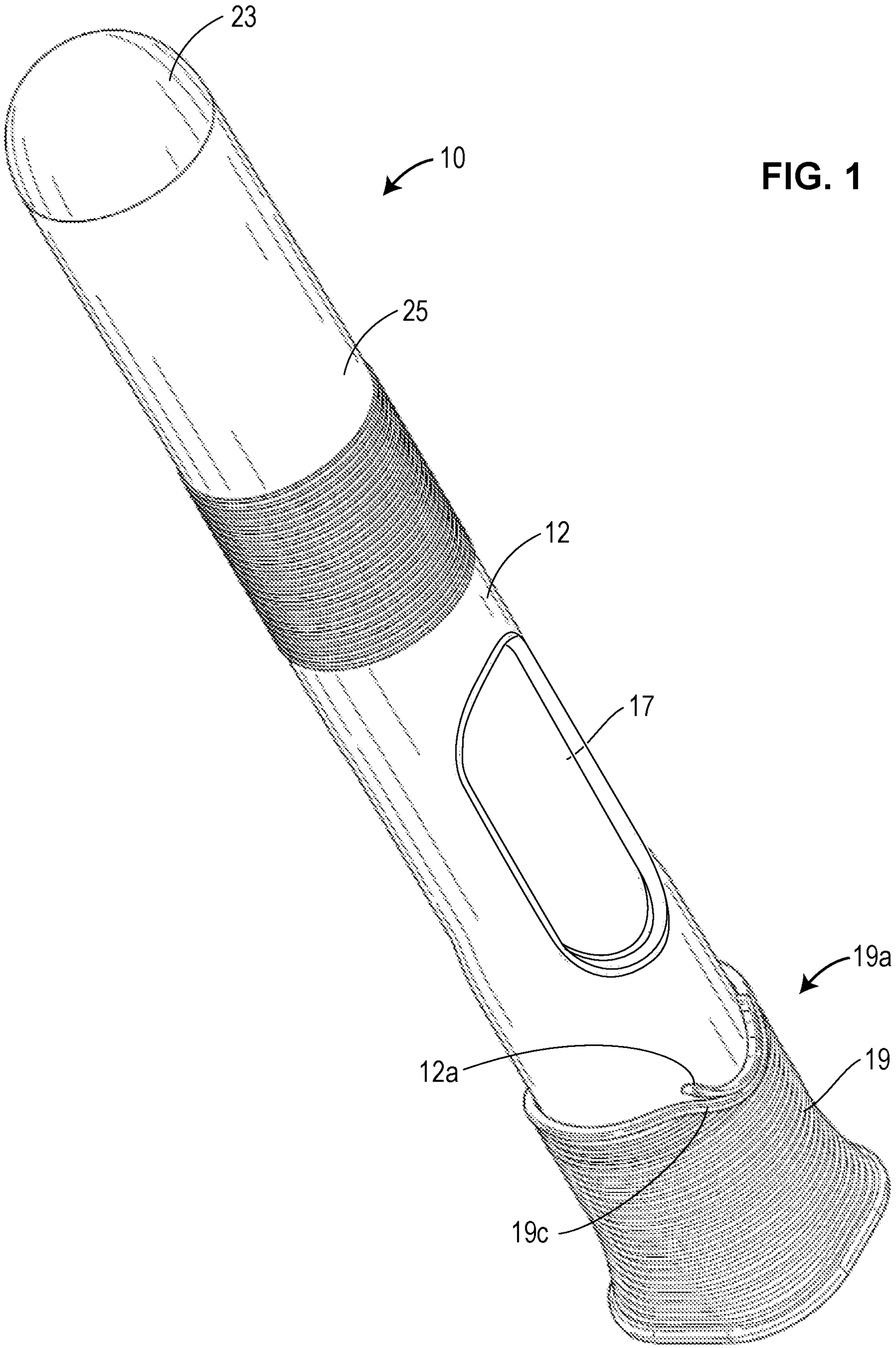
FIG. 1 is a perspective view of an exemplary drug delivery device in accordance with various embodiments, with a removable cap present and coupled with a housing.
Figure 2:
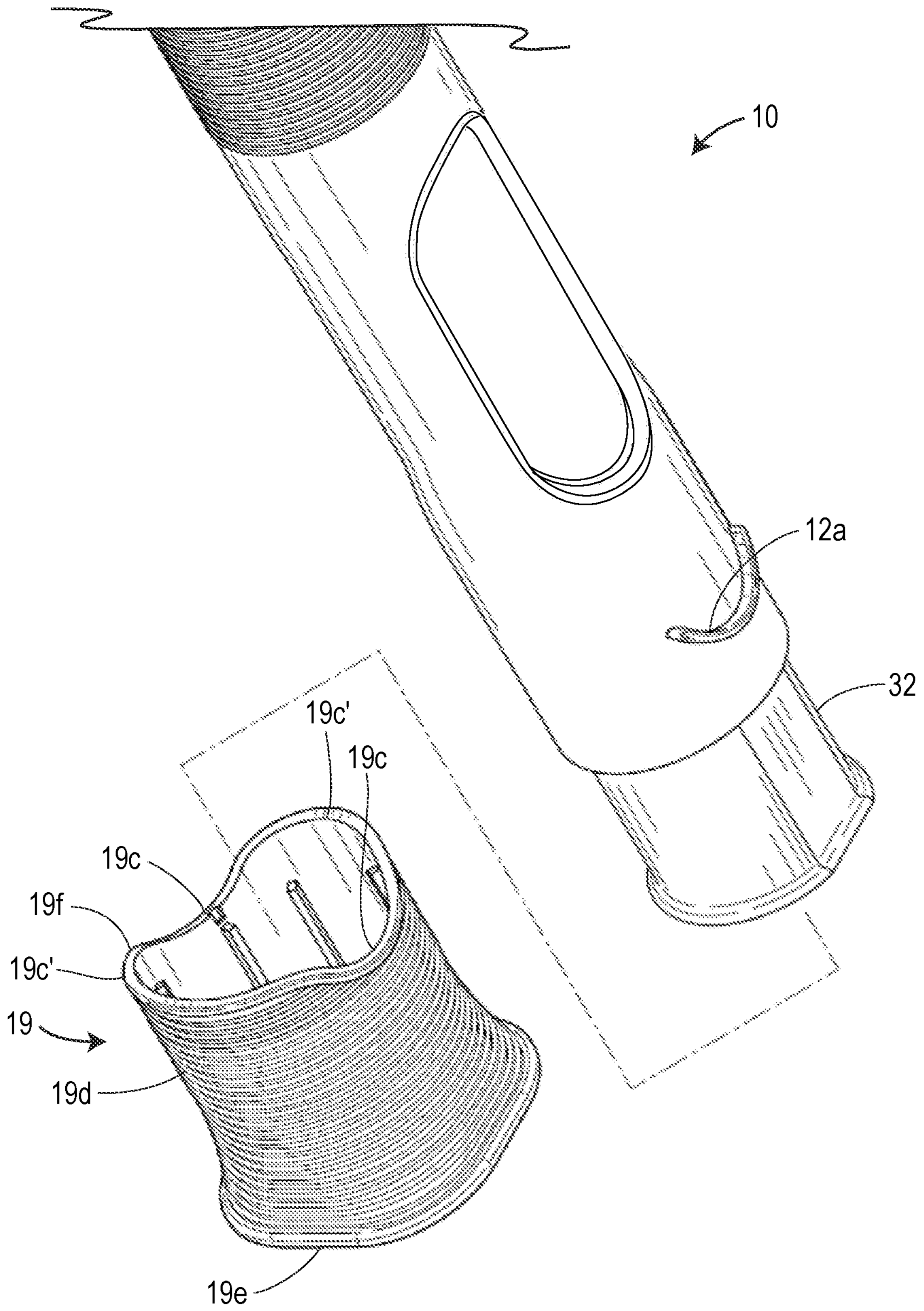
FIG. 2 is a perspective view of a distal portion of the drug delivery device in FIG. 1, with the removable cap removed therefrom.
Figure 3:
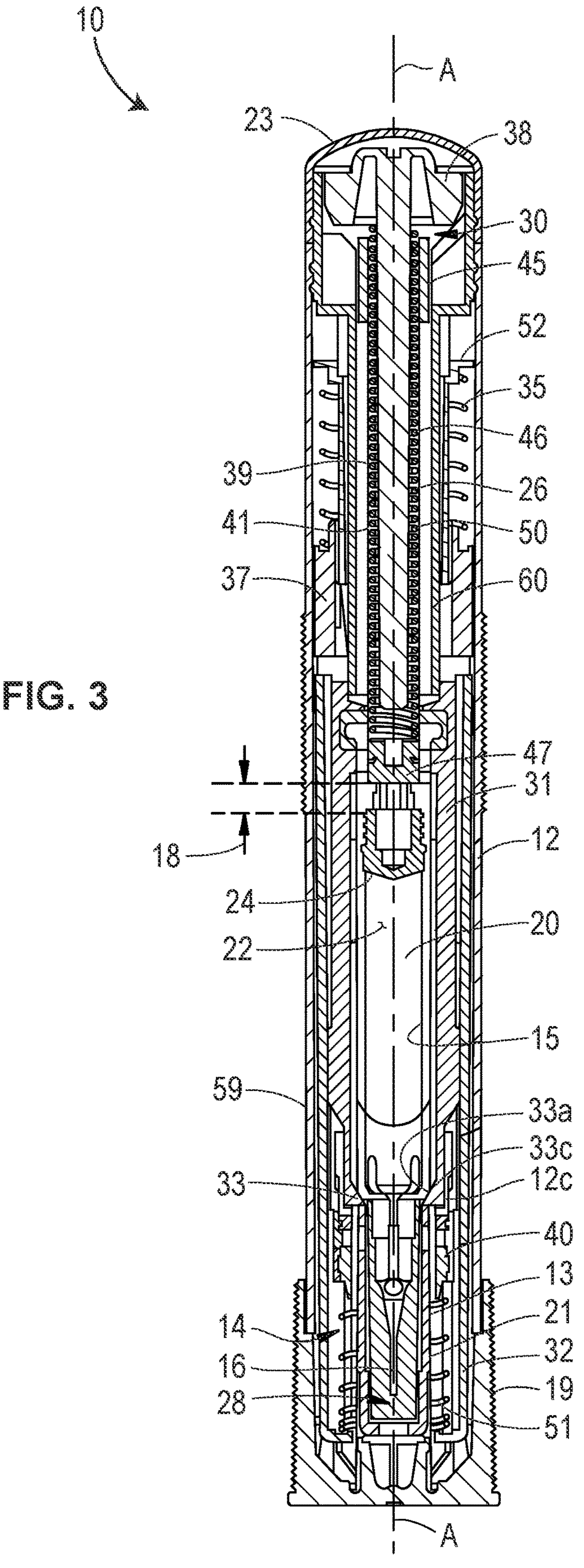
FIG. 3 is cross-sectional view of the drug delivery device in FIG. 1.

FIGS. 1-3 illustrate several views of an embodiment of a drug delivery device 10 for delivering a drug, which may also be referred to herein as a medicament or drug product. The drug may be, but is not limited to, various biologics such as peptides, peptibodies, or antibodies. The drug may be in a fluid or liquid form, although the present disclosure is not limited to a particular state.

Various implementations and configurations of the drug delivery device 10 are possible. The present embodiment of the drug delivery device 10 is configured as a single-use, disposable injector. In other embodiments, the drug delivery device 10 may be configured as multiple-use reusable injector. The drug delivery device 10 is operable for self-administration by a patient or for administration by caregiver or a formally trained healthcare provider (e.g., a doctor or nurse). The exemplary the drug delivery devices shown in the figures may take the form of an autoinjector or pen-type injector, and, as such, may be held in the hand of the user over the duration of drug delivery, but may also or alternatively be suitable for other drug delivery devices and/or configurations.

The configuration of various components included in the drug delivery device 10 may depend on the operational state of the drug delivery device 10. The drug delivery device 10 may have a storage state, a pre-delivery state, a delivery or dosing state, and a post-delivery state, although fewer or more states are also possible. For example, each state may have several sub-states or stages. The storage state may correspond to the configuration of the drug delivery device 10 in FIGS. 1-3, where the delivery device includes a removable cap in a storage position. In some embodiments, the storage state may exist in the time between when the drug delivery device 10 leaves a manufacturing facility and when a patient or other user removes the removable cap. The pre-delivery stage may correspond to the configuration of the drug delivery device 10 after the removable cap has been removed but prior to activation of a drive mechanism by the user. This may include the moments in time after the user has removed the removable cap, while the user is first positioning the drug delivery device 10 against the injection site, but before dosing has begun. The delivery state may correspond to the configuration of the drug delivery device 10 while drug delivery, also referred to herein as dosing, is in progress. The post-delivery state may correspond to the configuration of the drug delivery device 10 after drug delivery is complete and/or when a stopper is arranged in an end-of-dose position in a drug storage container.

Referring to FIGS. 1-3, the drug delivery device 10 includes an outer casing or housing 12. In some embodiments, the housing 12 may be sized and dimensioned to enable a person to grasp the injector 10 in a single hand. The housing 12 may have a generally elongate shape, such as a cylindrical shape, and extend along a longitudinal axis A between a proximal end and a distal end. An opening 14 (FIG. 3) may be formed in the distal end to permit an insertion end 28 of a delivery member 16 to extend outside of the housing 12. A transparent or semi-transparent inspection window 17 may be positioned in a wall of the housing 12 to permit a user to view component(s) inside the drug delivery device 10, including a drug storage container 20. Viewing the drug storage container 20 through the window 17 may allow a user to confirm that drug delivery is in progress and/or complete. A removable cap 19 may cover the opening 14 at the distal end of the device prior to use of the drug delivery device 10, and, in some embodiments, may include a gripper 13 (FIG. 3) configured to assist with removing a removable sterile barrier 21 (e.g., a rigid needle shield (RNS), a non-rigid needle shield (nRNS), etc.) mounted on the insertion end 28 of the delivery member 16. The gripper 13 may include one or more inwardly protruding barbs or arms that frictionally or otherwise mechanically engage the removable sterile barrier 21 to pull the removable sterile barrier 21 with the removable cap 19 when the user separates the removable cap 19 from the housing 12. Thus, removing the removable cap 19 has the effect of removing the removable sterile barrier 21 from the delivery member 16.

In some embodiments, the housing 12 may include two separate and interconnected structures: a rear end cap 23 (e.g., a rear cover) at the proximal end of the drug delivery device 10; and a tubular housing 25 extending substantially completely along the length of the drug delivery device 10 and defining the opening 14. Additionally or alternatively, the housing 12 may include fewer or more components, such as a two-piece tubular housing having front and rear portions. The tubular housing 25 may have a hollow and generally cylindrical or tubular shape, and the rear end cap 23 may have a generally hemispherical shape or a hollow cylindrical shape with an open end and a closed off end. In some embodiments, the rear end cap 23 and the tubular housing 25, and any components to be positioned therein, may be assembled together to define different sub-assemblies. In alternative embodiments, the housing 12 may be constructed in one piece, such that the housing 12 is defined by a single, monolithic structure that integrates a rear cap and tubular housing in a single component.

The drug storage container 20 is disposed within an interior space of the housing 12 and is configured to contain a drug. The drug storage container 20 may be pre-filled and shipped, e.g., by a manufacturer, to a location where the drug storage container 20 is combined with a remainder of the drug delivery device 10. For example, the drug 22 may be distributed and/or provided to patients in more than one use case, such as a as a pre-filled syringe or as an autoinjector including a pre-filled syringe. By utilizing the same or similar syringe components in either case, at least some of above steps such as filling, labeling, packaging, shipping, and distribution may be streamlined or simplified for two different use cases. As another example, in the event that multiple use cases utilize some or all of the same syringe components, some regulatory pathways to marketing and/or distributing the drug may be streamlined and/or simplified for at least one of the multiple use cases.

The drug storage container 20 may include a rigid wall defining an internal bore or reservoir. The wall may be made of glass or plastic. A stopper 24 may be moveably disposed in the drug storage container 20 such that it can move in a distal direction along the longitudinal axis A between proximal end and a distal end of the drug storage container 20. The stopper 24 may be constructed of rubber or any other suitable material. The stopper 24 may slidably and sealingly contact an interior surface 15 of the wall of the drug storage container 20 such that the drug 22 is prevented or inhibited from leaking past the stopper 24 when the stopper 24 is in motion. Distal movement of the stopper 24 expels the drug 22 from the reservoir of the drug storage container 20 into the delivery member 16. The proximal end of the drug storage container 20 may be open to allow a plunger 26 to extend into the drug storage container 20 and push the stopper 24 in the distal direction. In the present embodiment, the plunger 26 and the stopper 24 are initially spaced from each other by a gap 18. Upon activation of a drive mechanism 30, the plunger 26 moves in the distal direction to close the gap 18 and comes into contact with the stopper 24. Subsequent distal movement of the plunger 26 drives the stopper 24 in the distal direction to expel the drug 22 from the drug storage container 20. In alternative embodiments, the stopper 24 and the plunger 26 may initially be in contact with one another or coupled to one another, e.g., via a threaded coupling, such that they move together jointly from the start of movement of the plunger 26. Once the stopper 24 is in motion, it may continue to move in the distal direction until it contacts a proximally-facing portion of the interior surface 15 of the wall of the drug storage container 20. This position of the stopper 24 may be referred to as the end-of-dose or end-of-delivery position, and may correspond to when delivery of the drug 22 to the patient is complete or substantially complete.

In some embodiments, a volume of the drug 22 included in the reservoir of the drug storage container 20 may be equal to 1 mL, or equal to approximately (e.g., ±10%) 1 mL, or equal to 2.5 mL, or equal to approximately (e.g., ±10%) 2.5 mL, or equal to 3 mL, or equal to approximately (e.g., ±10%) 3 mL, or less than or equal to approximately (e.g., ±10%) 1 mL, or less than or equal to approximately (e.g., ±10%) 2 mL, or less than or equal to approximately (e.g., ±10%) 3 mL, or less than or equal to approximately (e.g., ±10%) 4 mL, or less than approximately (e.g., ±10%) 5 mL, or less than or equal to approximately (e.g., ±10%) 10 mL, or within a range between approximately (e.g., ±10%) 1-10 mL, or within a range between approximately (e.g., ±10%) 1-5 mL, or within a range between approximately (e.g., ±10%) 1-4 mL, or within a range between approximately (e.g., ±10%) 1-3 mL, or within a range between approximately (e.g., ±10%) 1-2.5 mL.

The delivery member 16 is connected or operable to be connected in fluid communication with the reservoir of the drug storage container 20. A distal end of the delivery member 16 may define the insertion end 28 of the delivery member 16. The insertion end 28 may include a sharpened tip of other pointed geometry allowing the insertion end 28 to pierce the patient's skin and subcutaneous tissue during insertion of the delivery member 16. The delivery member 16 may be hollow and have an interior passageway. One or more openings may be formed in the insertion end 28 to allow drug to flow out of the delivery member 16 into the patient.

In one embodiment, the drug storage container 20 may be a pre-filled syringe and has a staked, hollow metal needle for the delivery member 16. Here, the needle is fixed relative to the wall of the drug storage container 20 and may be in permanent fluid communication with the reservoir of the drug storage container 20. In other embodiments, the needle may be coupled to the drug storage container 20 via a Luer Lock or other suitable connection. In yet other embodiments, the drug storage container 20 may be a needle-less cartridge, and, as such, initially may not be in fluid communication with the delivery member 16. In such embodiments, the drug storage container 20 may move toward a proximal end of the delivery member 16, or vice versa, during operation of the drug delivery device 10 such that the proximal end of the delivery member 16 penetrates through a septum covering an opening in the drug storage container 20 thereby establishing fluid communication between the reservoir of the drug storage container 20 and the delivery member 16.

The device may also include a container holder 33 configured to secure the drug storage container 20 with respect to the housing 12, such as by preventing distal movement of the drug storage container 20 during actuation of the plunger. The container holder 33 may include a plurality of flanges **33*c* that each include an arcuate, sloped surface 33*a* that substantially matches the arcuate shape of a shoulder portion of the drug storage container 20. As a more specific example, when the drug storage container 20 is inserted within the container holder 33, the flanges 33*c* cooperate to support the shoulder portion and limit the travel of the drug storage container 20 in the distal direction. The housing 12 may include a plurality of lock slots 12*c* that each receive respective flanges 33*c* of the container holder 33 to prevent and/or restrict relative movement between the respective components 12, 33. As a result, when fully assembled the storage container 20, the container holder 33, and the housing 12** are all substantially or completely fixed with respect to each other.

The drug delivery device 10 may further include a guard mechanism for preventing contact with the insertion end 28 of the delivery member 16 when the drug delivery device 10 is not being used to administer an injection. The guard mechanism may include a guard member 32 moveably disposed at the distal end of the housing 12 adjacent to the opening 14. The guard member 32 may have a hollow and generally cylindrical or tubular shape centered generally about the longitudinal axis A, and may have a proximal end received within the housing 12. The guard member 32 may be configured to move relative to the housing 12 between an extended position wherein a distal end of the guard member 32 extends through the opening 14 in the housing 12 and a retracted position wherein the distal end of the guard member 32 is retracted, fully or partially, into the opening 14 in the housing 12. Additionally or alternatively, the guard member 32 may be configured to move from the retracted position to the extended position. When moving from the extended position to the retracted position, the guard member 32 may translate linearly in the proximal direction; and when moving from the retracted position to the extended position, the guard member 32 may translate linearly in the distal direction. In at least the extended position, the guard member 32 may extend beyond and surround the insertion end 28 of the delivery member 16. In embodiments where the delivery member 16 protrudes from the opening 14 in the housing 12 in the pre-delivery or storage state, moving the guard member 32 from the extended position to the retracted position, e.g., by pressing the distal end of the guard member 32 against the patient's skin at the injection site, may result in the insertion end 28 of the delivery member 16 being inserted into the patient's skin.

The guard mechanism may further include a guard biasing member 35 and a guard extension 37. The guard extension 37 may be positioned proximal to the guard member 32; and the guard biasing member 35 may be positioned proximal to the guard extension 37. The guard extension 37 may have a hollow and generally cylindrical or tubular shape centered about the longitudinal axis A. Furthermore, the guard extension 37 may be moveable in a linear direction along the longitudinal axis A relative to the housing 12. In the present embodiment, the guard extension 37 is a separate structure from the guard member 32. However, in alternative embodiments, the guard extension 37 and the guard member 32 may be integrally formed in one piece to define a single, monolithic structure. In such alternative embodiments, the proximal end of the guard member 32 may correspond to the guard extension 37.

The guard biasing member 35 may be positioned between and in contact with the guard extension 37 and a releaser member 52. The guard biasing member 35 may be configured to bias or urge the guard extension 37 in the distal direction and bias or urge the releaser member 52 in the proximal direction. The guard biasing member 35 may initially be in an energized (e.g., compressed) state such that it exerts a biasing force on the guard extension 37 and a biasing force on the releaser member 52 in the pre-delivery state. In some embodiments, a distal end of the guard extension 37 is initially in contact with a proximal end of the guard member 32, as seen in FIG. 3. As a consequence, the guard extension 37 transfers a biasing force of the guard biasing member 35 to the guard member 32, such that the guard biasing member 35 biases or urges the guard member 32 toward the extended position. A user may overcome the biasing force by pressing the guard member 32 against the injection site. In doing so, the guard member 32 and the guard extension 37 move jointly in the proximal direction until, for example, the guard member 32 reaches the retracted position. When the injection is complete and the drug delivery device 10 is lifted off of the injection site, the guard biasing member 35 may push the guard extension 37 so that the guard extension 37 and the guard member 32 move jointly in the distal direction. This motion returns the guard member 32 to the extended position, which has the effect of covering the insertion end 28 of the deliver member 16. In some embodiments, the guard biasing member 35 may include a compression spring (e.g., a helical compression spring). Furthermore, in embodiments where the plunger biasing member 50 also includes a compression spring, the guard biasing member 35 may disposed around and/or have a larger diameter than the plunger biasing member 50.

After drug delivery is complete and the guard member 32 has been re-deployed to the extended position, it may be desirable to lock the guard member 32 in the extended position to prevent subsequent user contact with the insertion end 28 of the delivery member 16 and/or to prevent re-use of the drug delivery device 10. Pursuant to these ends, some embodiments of the drug delivery device 10 may include a lock ring 40 configured to selectively rotate, depending on the axial position of the guard member 32, in order to lock the guard member 32 in the extended position once the guard member 32 has moved from the retracted position to the extended position. In the present embodiment, the lock ring 40 is centered and rotates about the longitudinal axis A. As illustrated in FIG. 3, a proximal end of the lock ring 40 may be in contact with the container holder 33 and the distal end of the lock ring 40 may be disposed at least partially within the guard member 32. The lock ring biasing member 51 may be positioned in the axial direction between a distally facing surface of the lock ring 40 and a proximally facing surface of the guard member 32. The lock ring biasing member 51 may initially be in a compressed or energized state such that it biases the lock ring 40 and the guard member 32 away from each other. As such, the lock ring biasing member 51 may exert a biasing force urging the guard member 32 toward the extended position, as well as exert a biasing force urging the proximal end of the lock ring 40 against the container holder 33. In some embodiments, the lock ring biasing member 51 may include a compression spring (e.g., a helical compression spring). In some embodiments, rotation of the lock ring 40 may be achieved by a camming arrangement between the lock ring 40 and the container holder 33.

The drug delivery device 10 may further include a drive mechanism 30 disposed partially or entirely within the housing 12. Generally, the drive mechanism 30 may be configured to store energy and, upon or in response to activation of the drive mechanism 30 by the user, release or output that energy to drive the plunger 26 to expel the drug 22 from the drug storage container 20 through the delivery member 16 into the patient. In the present embodiment, the drive mechanism 30 is configured to store mechanical potential energy; however, alternative embodiments of the drive mechanism 30 may be configured differently, for example, with the drive mechanism 30 storing electrical or chemical potential energy. Generally, upon activation of the drive mechanism 30, the drive mechanism 30 may convert the potential energy into kinetic energy for moving the plunger 26.

In the present embodiment, the drive mechanism 30 includes the plunger biasing member 50, a plunger biasing member seat 38, the releaser member 52, and a plunger guide 60. The plunger biasing member 50 may include a compression spring (e.g., a helical compression spring) which is initially retained in an energized state. In the energized state, the plunger biasing member 50 may be compressed such that its axial length is shorter than it would be in a natural or de-energized state. When released, the plunger biasing member 50 may try to expand to its natural axial length, and as a consequence, exert a biasing force pushing the plunger 26 in the distal direction.

The plunger biasing member 50 may be disposed at least partially within the plunger 26, and may have a distal end abutting against a proximally facing inner surface of the plunger 26 and/or may be fixedly attached to an inner surface of the plunger 26. So that the plunger biasing member 50 may be received within the plunger 26, an outer diameter or other dimension of the plunger biasing member 50 may be equal to or less than an inner diameter of the a ring 45 and/or equal to or less than an inner diameter of the hollow rod 46. In some embodiments, the distal end of the plunger biasing member 50 may abut against a proximally facing inner surface of the base 47 of the plunger 26. Furthermore, a proximal end of the plunger biasing member 50 may abut against a distally facing surface of the plunger biasing member seat 38. The plunger biasing member seat 38 may be fixedly attached to the tubular housing 25 such that the plunger biasing member seat 38 provides a stationary surface for the plunger biasing member 50 to push off of. So configured, the plunger biasing member 50, when released from the energized state, may expand in length with distal end of the plunger biasing member 50 moving in the distal direction away from the stationary proximal end of the plunger biasing member 50. This motion may push the plunger 26 is the distal direction, which, in turn, may push the stopper 24 in the distal direction to expel the drug 22 from the drug storage container 20 into the delivery member 16 and thereafter into the patient.

The releaser member 52 may have a hollow and generally cylindrical or tubular shape, and may be centered about the longitudinal axis A. As illustrated in FIG. 3, the releaser member 52 may be positioned in the radial direction between the distal end of the plunger guide 60 and a proximal end of the guard extension 37. Furthermore, the releaser member 52 may be arranged radially inwardly of the guard biasing member 35. Generally, the releaser member 52 is configured to operably couple the guard member 32 and the plunger 26 in an activation sequence and to generate an audible signal indicating the end of drug delivery. So configured, the releaser member 52 is exploited to perform two separate functions, and thus reduces the number of moving parts required by the drug delivery device 10.

The releaser member 52 may be configured to rotate relative to the housing 12 and/or translate linearly relative to the housing 12, depending on the stage of operation of the drug delivery device 10. Initial rotation of the releaser member 52 associated with activation may be powered by the plunger biasing member 50 and/or the guard biasing member 35; whereas later rotation of the releaser member 52 associated with generation of the end-of-dose signal may be powered solely by the guard biasing member 35. Any linear translation of the releaser member 52 without rotation may be powered solely by the guard biasing member 35. In some embodiments, the releaser member 52 may translate linearly only in the proximal direction; however, alternative embodiments may permit linear translation of the releaser member 52 in both the proximal and distal directions.

An ability of the releaser member 52 to rotate about the longitudinal axis A may be regulated by an interaction between an outer portion of an annular wall of the releaser member 52 and an inner portion of the guard extension 37. The guard extension 37 may be prevented from rotating about the longitudinal axis A as a consequence of its coupling to the housing 12. This has the effect of preventing rotation of the releaser member 52 about the longitudinal axis A when abutment structures (e.g., outwardly extending projections) included on the outer portion of the releaser member 52 engage cooperating abutment structures (e.g., inwardly extending projections) included on the inner portion of the guard extension 37. If the releaser member 52 is unable rotate, an outwardly extending projection of the plunger 26 received in a recess formed in the inner surface of the releaser member 52 is also unable to rotate. If this projection on the plunger 26 cannot rotate, then it cannot slide into a longitudinal opening in the plunger guide 60. If the projection cannot move in this manner, then plunger 26 also cannot move. If the plunger 26 cannot move, the plunger biasing member 50 cannot expand and de-energize. Thus, the releaser member 52 retains the plunger biasing member 50 in the energized state until the guard extension 37 moves to an axial position where the cooperating abutment structures on the outer portion of the releaser member 52 and the inner portion of the guard extension 37 disengage from each and thereby permit the releaser member 52 to rotate relative to the guard extension 37.

As discussed above, the removable cap 19 may have a storage position (FIGS. 1 and 3) where the removable cap 19 is coupled with the housing 12 and a removed position (FIG. 2) where the removable cap 19 is removed from and not coupled with the housing 12. As also discussed above, the device 10 may include a removable sterile barrier 21 that is removed from the delivery member 16 when the removable cap 19 is removed from the housing 12. The removable sterile barrier 21 may have a relatively snug or relatively high-friction fit with the drug storage container 20 to maintain the sterility of the delivery member 16 and/or to prevent air from entering the drug storage container 20. For example, in order to reduce the likelihood of contamination and/or occlusions or evaporated drug, it may be desirable to prevent or reduce the likelihood of air entering the drug storage container and/or the delivery member 16. Additionally or alternatively, it may be desirable to have a relatively snug or relatively high-friction fit between the sterile barrier 21 and the drug storage container 20 to prevent or reduce the likelihood of inadvertent needle sticks. For these or other reasons, it may also or alternatively be desirable to have a relatively snug or relatively high-friction fit between the removable cap 19 and the housing 12. The sterile barrier 21 and the removable cap 19 may also be coupled with their respective components (e.g., drug storage container 20 and housing 12) via other suitable features, such as coupling tab/slot connections, breakable connections such as perforated seals, threaded connections, or other features that achieve relatively secure but removable connections between respective components.

As a result of these coupling forces, features, and/or other factors, some device users may experience difficulty or discomfort removing the removable cap 19. As an example, some device users may have difficulty removing the cap 19 via axial forces alone (along longitudinal axis A). In other words, some device users may have difficulty in pulling the cap 19 off of/away from the housing 12. The cap 19 shown in Figs. FIGS. 1-3 includes a plurality of ribs **19*d* to help the user grip the surface of the removable cap 19** when removing the same.

The device 10 shown in FIGS. 1-3 also includes camming features to translate rotational motion into axial motion such that, upon rotational movement of the removable cap 19, the removable cap 19 is urged away from the housing 12, thereby facilitating and/or easing removal of the cap 19. For example, the housing 12 includes a housing camming feature **12*a* and a cap camming feature 19*c*. As a more specific example, to remove the removable cap 19 from the housing 12 via axial force/movement only (e.g., "straight-pull force"), a user may be required to exert 45 Newtons or less; approximately 40 to 45 Newtons; approximately 35 to 40 Newtons; approximately 30 to 35 Newtons; approximately 25 to 30 Newtons; approximately 20 to 25 Newtons; approximately 15 to 20 Newtons; approximately 10 to 15 Newtons; approximately 5 to 10 Newtons; or less than approximately 5 Newtons. In the device 10 shown in FIGS. 1-3, removing the removable cap 19** requires approximately 10 to 15 Newtons of straight-pull force.

The cap camming feature 19*c* shown in FIGS. 1-3 defines a wave shape, such as an arc-shaped surface. As a more specific example, the removable cap 19 shown in the figures includes a generally cylindrical body portion 19*d* and an end wall 19*e* that is generally perpendicular to the body portion 19*d* at the distal end of the cap 19. The body portion 19*d* defines a generally annular leading rim 19*f* at the proximal end of the cap 19. The leading rim 19*f* defines the wave shaped cap camming feature 19*c*. As an even more specific example, the leading rim 19*f* shown in the figures defines two wave shaped camming surfaces 19*c* and two relatively flat surfaces 19*c*' that extend between wave shaped camming surfaces 19*c*. In other words, the two wave shaped camming surfaces 19*c* and the two relatively flat surfaces 19*c*' cooperate to define the leading rim 19*f*. Alternatively, the leading rim 19*f* may define a continuous wave shape such as a continuous sinusoidal wave or another continuous wave shape. For the purposes of this application, the term "continuous" should be interpreted to mean that the wave shape continues around the entire perimeter of the leading edge rather than alternating wave shaped and flat surfaces The housing camming feature 12*a* shown in FIGS. 1-3 defines a wave shape, such as an arc-shaped protrusion extending away from the outer surface 25 of the housing 12. As a more specific example, the housing camming feature 12*a* is a protrusion having a shape that is not unlike a "smile" or a "crescent moon" shape. As an even more specific example, the housing 12 shown in the figures defines two wave shaped camming features 12*a*.

When the removable cap 19 is in the storage position 19*a* shown in FIGS. 1-3, the cap camming features 19*c* engage or abut the housing camming features 12*a*. Additionally, the respective camming features 12*a*, 19*c* shown in the figures have matching or mirrored shapes such that the respective surfaces 12*a*, 19*c* slide smoothly/easily across each other. For example, when the removable cap 19 is rotated (either clockwise or counterclockwise) with respect to the housing 12, the housing camming features 12*a*, 19*c* rotate with respect to each other and urge the removable cap 19 away from the housing 12 along axis A. In other words, the camming features 12*a*, 19*c* translate rotational motion into axial motion to remove or assist with removal of the cap 19. In some embodiments, even a relatively small rotation may facilitate and/or ease removal of the cap 19.

Having described the general configuration of the drug delivery device 10, a general method of using the drug delivery device 10 to perform an injection will now be described. As a preliminary step, the user may remove the drug delivery device 10 from any secondary packaging, such as a plastic bag and/or cardboard box. Also, as a preliminary step, the user may prepare the injection site, e.g., by rubbing the patient's skin with an alcohol wipe. Next, the user may pull and detach the removable cap 19 from the housing 12, as described below in more detail. As a result of this motion, the gripper 13 may pull and detach the removable sterile barrier 21 from the drug storage container 20. This may uncover the insertion end 28 of the delivery member 16. Nevertheless, the insertion end 28 of the delivery member 16 will remain surrounded by the guard member 32 at this stage because the guard member 32 is arranged in the extended position. Next, the user may position the drug delivery device 10 over the injection site and then push the distal end of the guard member 32 against the injection site. The force applied by the user will overcome the biasing force of the guard biasing member 35 and the biasing force of the lock ring biasing member 51, thereby causing the guard member 32 to retract into the opening 14 moving from the extended position to the retracted position in the proximal direction. The delivery member 16 remains stationary relative to the housing 12 during the retracting movement of the guard member 32.

Movement of the guard member 32 from the extended position to the retracted position may cause several actions to occur. Because the delivery member 16 remains stationary relative to the housing 12 during retraction of the guard member 32, the insertion end 28 of the delivery member 16 is caused to extend through an opening in the distal end of the guard member 32, thereby piercing the patient's skin at the injection site and penetrating into the patient's subcutaneous tissue. In addition, retraction of the guard member 32 may also activate the drive mechanism 30 to expel the drug 22 from the drug storage container 20.

When the guard member 32 moves from the extended position to the retracted position, the guard member 32 may push the guard extension 37 in the proximal direction. During proximal movement of the guard extension 37, the above-mentioned cooperating abutment structures on the outer portion of the releaser member 52 and the inner portion of the guard extension 37 may slide past one another until they are no longer in contact with one another. When that occurs, the releaser member 52 may be free to rotate about the longitudinal axis A. Rotation of the releaser member 52 at the present stage is caused by the plunger biasing member 50 expanding and pushing a distally facing camming surface included in on the plunger 26 to slide along a proximally facing camming surface on the plunger guide 60. The resulting camming action causes the plunger 26 to rotate, which, in turn, may cause the releaser member 52 to jointly rotate.

Joint rotation of the releaser member 52 and the plunger 26 may continue until the distally facing camming surface included in on the plunger 26 reaches the end of the proximally facing camming surface on the plunger guide 60 and moves into a longitudinal slot formed in the plunger guide 60. The longitudinal slot does not inhibit linear movement of the plunger 26. As consequence, the plunger 26 is driven by the expanding plunger biasing member 50 to translate linearly in the distal direction. As a consequence, the plunger 26 comes into contact with the stopper 24 (if it is not already in contact with the stopper 24) and thereafter pushes the stopper 24 in the distal direction to expel the drug 22 from the drug storage container 20 through the delivery member 16 and out of the insertion end 28 into the patient's tissue. Drug delivery may carry on until the stopper 24 reaches the end-of-dose position. Here, the stopper 24 may abut against a proximally facing portion of the interior surface 15 of the wall of the drug storage container 20. As a result, the plunger 26 ceases moving in the distal direction.

After delivery is complete, the user may then lift the drug delivery deice 10 off of the injection site. With nothing to resist it, the guard biasing member 35 may push the guard member 32 from the retracted position to the extended position to cover the insertion end 28 of the delivery member 16. In some embodiments, this movement of the guard member 32 may cause the lock ring 40 to rotate to a position where it prevents subsequent retraction of the guard member 32.

These and other aspects of an exemplary drug delivery device are discussed in more detail in U.S. patent application Ser. No. 17/036,690, filed Sep. 29, 2020, U.S. patent application Ser. No. 17/035,851, filed Sep. 29, 2020, U.S. patent application Ser. No. 17/035,927, filed Sep. 29, 2020, U.S. patent application Ser. No. 17/036,129, filed Sep. 29, 2020, U.S. patent application Ser. No. 17/036,217, filed Sep. 29, 2020, and US Provisional Patent Application entitled "DRUG DELIVERY DEVICE" filed by Applicant of the present application on the same day as the present application, the entire contents of each of which are incorporated by reference.

Turning to FIGS. 4-19, embodiments of the above-mentioned removable cap will now be described. Various elements of the removable cap 119 illustrated in FIGS. 4-19 may be similar or identical in structure, configuration, and/or function to elements of the removable cap 19 described above in conjunction with FIGS. 1-3. Such elements are assigned with the same reference numeral as used in FIGS. 1-3, except incremented by 100 or a multiple thereof. A description of some of these elements is abbreviated or eliminated in the interest of conciseness. Details of the structure, configuration, and/or function that differentiate the embodiments of the removable cap 119 illustrated in FIGS. 4-19 from the embodiment of the removable cap 19 in FIGS. 1-3 are the focus of the discussion below.

As described above, it may be advantageous to incorporate one or more shock absorbing features into the removable cap. In the event that the drug delivery device 10 is accidentally dropped from a height such that the removable cap contacts the ground with substantial velocity or the removable cap otherwise strikes or is struck with an external object with substantial velocity, the removable cap may experience substantial impulse force(s). Such force(s) have the potential to trigger the activation of automated or semi-automated features included in the drug delivery device 10 and/or cause damage to the drug delivery device 10. As an example, dropping the drug delivery device 10 with the longitudinal axis A parallel or substantially parallel to the direction of gravity and with the removable cap facing generally downwards may, due to the deceleration associated with the drug delivery device 10 striking the ground, cause the guard member 32 to retract into the housing, thereby potentially triggering the drive mechanism 30. Additionally or alternatively, the deceleration may cause the lock ring 40 to rotate or otherwise move to a position where it prevents subsequent retraction of the guard member 32. This, in turn, may prematurely lockout of the guard member 32, thereby preventing a user from using the drug delivery device 10 to perform an injection. If the drug delivery device 10 was recently removed from cold storage (e.g., a temperature at 10° C. or lower, at 5° C. or lower, or at 0° C. or lower) prior to being dropped, there may be a risk, due to, e.g., the reduced elasticity of certain materials at low temperatures, for component of the drug delivery device 10 to fracture or crack. Such fractures or cracks may compromise proper operation of the drug delivery device 10, and, even if they do not, if they are visible to the user, they may cause the user to assume that the drug delivery device 10 is defective and consequently discard the drug delivery device 10, which may or may not be necessary.

FIGS. 4-8 illustrate an embodiment of a removable cap 119 having shock absorbing characteristics to mitigate or eliminate the undesirable effects of a sudden externally applied force, as well as other advantageous characteristics. The cap 119 may have a generally elongate shape extending along the longitudinal axis A between a proximal end 162 and a distal end 164. As an example, the cap 119 may have a longitudinal axis that is parallel to and/or coaxial with the longitudinal axis A. The removable cap 119 may further include an outer portion 166 and an inner portion 168, with the outer portion 166 being farther away from the longitudinal axis A than the inner portion 168. As an example, the outer portion 166 may partially or entirely surround the inner portion 168. As a more specific example, the outer portion 166 and/or the inner portion 168 may be centered about the longitudinal axis A. The outer portion 166 may include at least a portion of the proximal end 162 and at least a portion of the distal end 164. The outer portion 166 may extend between and include at least a portion of the proximal end 162 and at least a portion of the distal end 164. The inner portion 168 may be arranged at the distal end 164, or, alternatively, may extend between and include at least a portion of the proximal end 162 and at least a portion of the distal end 164.

Figure 4:
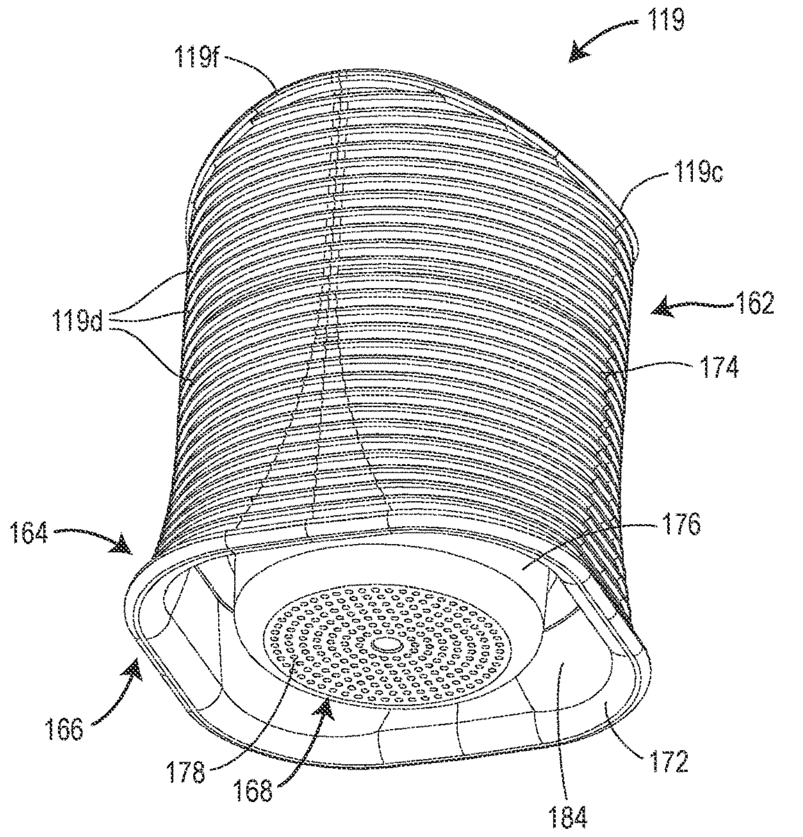
FIG. 4 is a perspective view of another exemplary removable cap in accordance with various embodiments.
Figure 5:
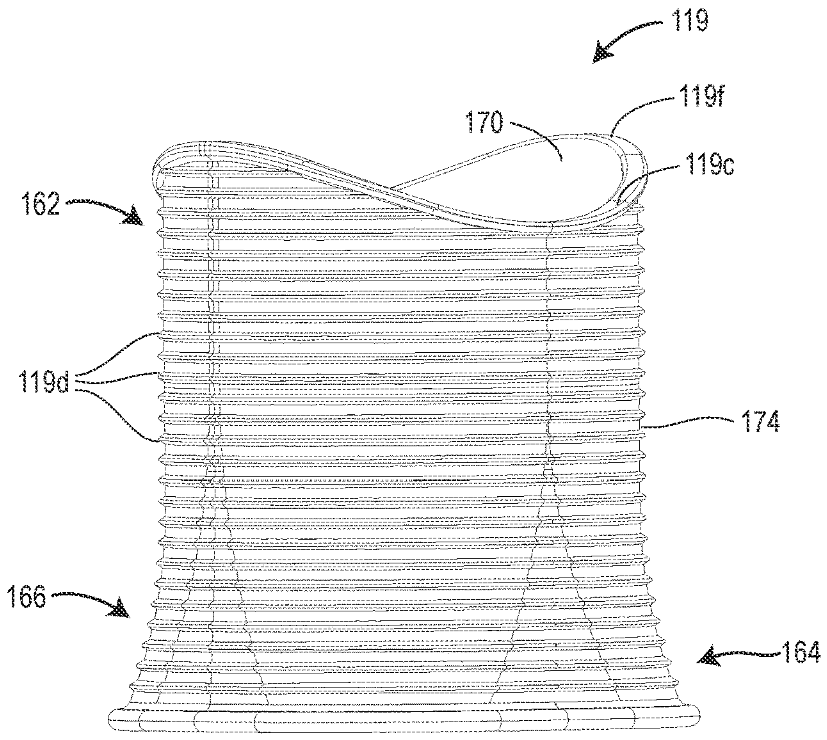
FIG. 5 is another perspective view of the removable cap in FIG. 4.

The proximal end 162 may include a first axial opening 170 (FIG. 6) and the distal end 164 may include a second axial opening 172 (FIG. 4). The outer portion 166 may partially or entirely surround the first axial opening 170 and/or the second axial opening 172. The inner portion 168 may be axially aligned with the first axial opening 170 and/or the second axial opening 172.

The proximal end 162 and/or the outer portion 166 of the removable cap 119 may be configured to be removably coupled with a housing of a drug delivery device (e.g., the housing 12 of the drug delivery device 10 described above) such that the removable cap 119 has a storage position where the removable cap 119 is coupled with the housing and at least partially covering an opening (e.g., the opening 14 described above) and a removed position where the removable cap 119 is not coupled with the housing. As an example, the first axial opening 170 may be sized to receive a distal end of the housing of the drug delivery device such that a relatively snug or relatively high-friction fit is formed between the proximal end 162 and/or the outer portion 166 of the removable cap 119 and the distal end of the housing when the removable cap 119 is in the storage position. Additionally or alternatively, the proximal end 162 and/or the outer portion 166 of the removable cap 119 may include one or more connector members configured to releasably couple with one or more connector members included on the distal end of the housing of the drug delivery device.

The outer portion 166 of the removable cap 119 may include an include a wall 174 having a generally annular shape (e.g., a tubular shape). As an example, the wall 174 may have a proximal end having a generally circular cross-section in a plane perpendicular to the longitudinal axis A and a distal end having a non-circular cross-section in a plane perpendicular to the longitudinal axis A. As a more specific example, the distal end of the wall 174 may have a generally square-shaped cross-section. As an even more specific example, the square-shaped cross-section of the distal end of the wall 174 may have rounded corners, as seen in FIGS. 4-8. The cross-section of the wall 174 may gradually transition from the circular cross-section to the square-shaped cross-section moving in a direction along the longitudinal axis A. The circular cross-section of the proximal end of the wall 174 may have an inner diameter sized to facilitate a relatively snug or relatively high-friction fit between the removable cap 119 and the housing of the drug delivery device. The square-shaped or other non-circular cross-section of the distal end of the wall 174 may inhibit or prevent the removable cap 119 from rolling across a flat surface such as a tabletop or countertop when the removable cap 119 and/or the drug delivery device (if the removable cap 119 is attached) is placed on its side on the flat surface.

The inner portion 168 of the removable cap 119 generally may be configured to assist with removing a removable sterile barrier (e.g., the removable sterile barrier 21 described above) mounted over an insertion end of a delivery member (e.g., a needle) of a drug storage container included in a drug delivery device. As an example, the inner portion 168 of the removable cap 119 may define or be coupled with a gripper (e.g., the gripper 13 described above) which is configured to engage the removable sterile barrier such that when the removable cap 119 is removed from the housing of the drug delivery device the gripper removes the removable sterile barrier from the drug storage container to uncover the insertion end of the delivery member. As a more specific example, the inner portion 168 and/or the gripper may rotate with respect to (i.e., rotate independently of) the removable sterile barrier when a user rotates the removable cap 119 with respect to the housing of the drug delivery device, and, when the removable cap 119 moves in the distal direction, the gripper may frictionally or otherwise mechanically engage the removable sterile barrier to pull the removable sterile barrier off of the drug storage container to expose the insertion end of the delivery member.

Figure 7:
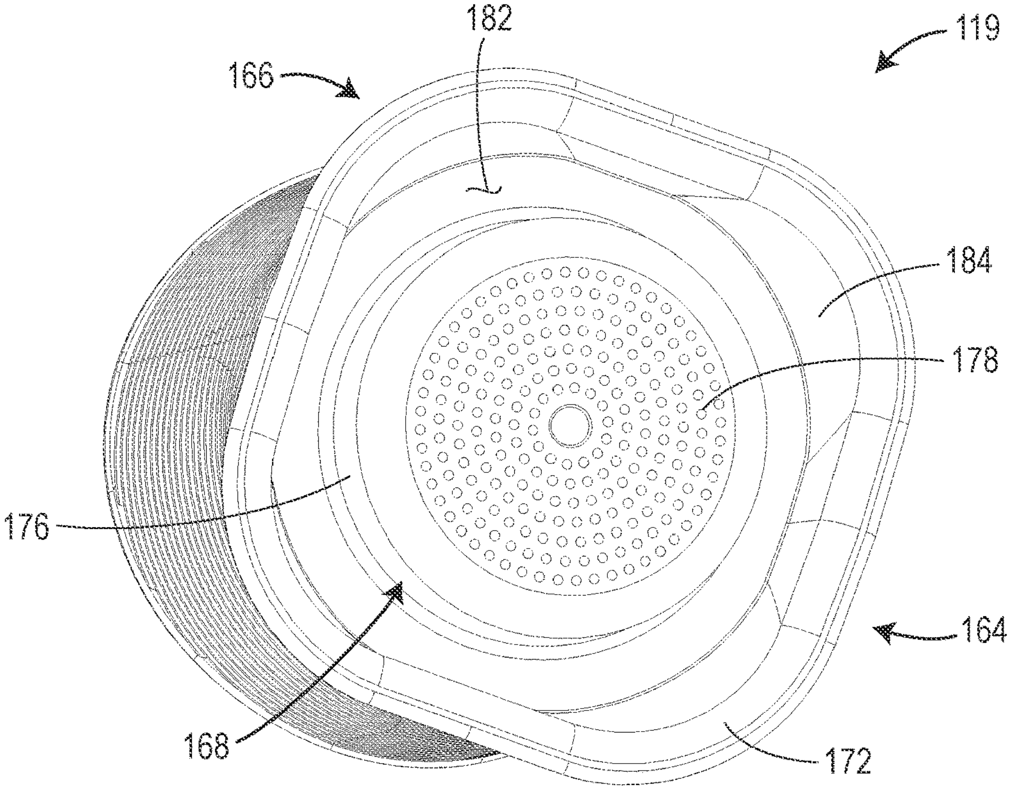
FIG. 7 is another perspective view of the distal end of the removable cap in FIG. 4.
Figure 8:
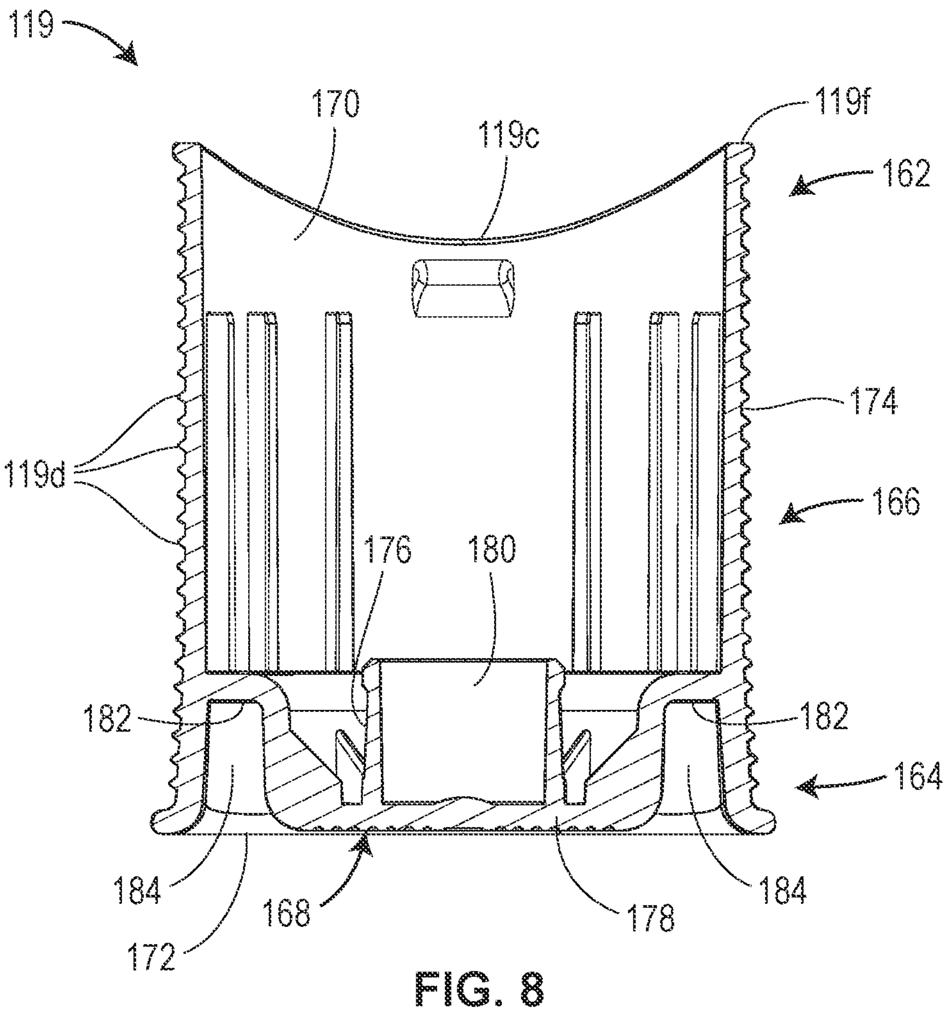
FIG. 8 is a cross-sectional view of the removable cap in FIG. 4.

Referring to FIGS. 4, 7, and 8, the inner portion 168 of the removable cap 119 may include a sidewall 176 that is generally parallel to the longitudinal axis A and a transverse wall 178 that is generally perpendicular to the longitudinal axis A. As an example, the sidewall 176 may have a generally annular shape to define a cavity 180 for receiving at least a distal end of the removable sterile barrier. The sidewall 176 may be defined by a single annular structure or alternatively a plurality of spaced apart structures arranged generally in circle or other annular shape. The inner surface of the sidewall 176 may define the gripper described above, or, alternatively, the gripper may be a separate structure that is coupled with and/or arranged inwardly of the sidewall 176. The transverse wall 178 may be coupled with a distal end of the sidewall 176. As an example, the transverse wall 178 may be coupled with the sidewall 176 to define a closed distal end of the inner portion 168.

The inner portion 168 of the removable cap 119 may be coupled with the outer portion 166 of the removable cap 119. As an example, the inner portion 168 may include a flange 182 extending radially outwardly from and fixedly connected to the proximal end of the sidewall 176 and fixedly connected to the wall 174 of the outer portion 166, as seen in FIGS. 7 and 8. As a more specific example, the flange 182 may be a wall that is generally perpendicular to the longitudinal axis A and covers a radial distance between the outer surface of the sidewall 176 of the inner portion 168 and the inner surface of the wall 174 of the outer portion 166 such that the flange 182 provides a barrier preventing physical access to the interior of the proximal end of the removable cap 119 when the removable cap 119 is removably coupled with the housing of a drug delivery device. In some embodiments, the wall 174, the sidewall 176, the transverse wall 178, and/or the flange 182 may be integrally formed in one piece to define a single, monolithic structure, but this is not required.

As described above, the flange 182 may be arranged radially between the proximal end of the inner portion 168 and the proximal or distal end of the outer portion 166. Distal to the flange 182, a gap 184 may separate the inner portion 168 and the outer portion 166, as seen in FIGS. 4, 7, and 8. As an example, the gap 184 may separate a distal end of the inner portion 168 and the distal end of the outer portion 166. As a more specific example, the gap 184 may be a radial gap such that there is empty space located radially between the distal end of the inner portion 168 and the distal end of the outer portion 166. The gap 184 may partially or entirely surround a circumference or periphery of the inner portion 168. The gap 184 may communicate with the second axial opening 172 and, in some embodiments, may be blocked off from the first axial opening 170 by the flange 182 such that the gap 184 does not communicate with the first axial opening 170. As a more specific example, the gap 184 may surround the entire circumference or periphery of the inner portion 168 such that the distal end of the wall 174 of the outer portion 166 defines a skirt-like structure surrounding the inner portion 168.

In the event that an external force is applied to the outer portion 166, the outer portion 166 may bend with respect to the inner portion 168, at least in part because of the gap 184. As an example, the gap 184 may provide space and/or freedom for at least a portion of the outer portion 166 to bend: radially inwardly toward the longitudinal axis A, radially outwardly away from the longitudinal axis A, in the proximal direction, and/or in the distal direction. The term "bend" as used herein is a broad term and is to be given its ordinary and customary meaning to a person of ordinary skill in the art (and is not to be limited to a special or customized meaning) and furthermore refers without limitation to any elastic and/or non-elastic deformation, deflection, and/or flexing that an object may undergo when subjected to an external force or load.

As an example, the removable cap 119 may be subjected to an external force as a result of the drug delivery device including the removable cap 119 being dropped from a height onto a stationary surface such as the ground, a floor, a tabletop, a countertop, etc. As a more specific example, the drug delivery device may fall with the longitudinal axis A generally parallel or otherwise non-perpendicular to the direction of gravity and with a distally directed end surface of the removable cap 119 facing generally downwards. In such a scenario, the ground or other external surface may exert a reaction force on the removable cap 119 in a direction that is generally parallel or otherwise non-perpendicular to the longitudinal axis A. By comparison, if the drug delivery device falls with the longitudinal axis A generally perpendicular or otherwise non-parallel to the direction of gravity, the ground or other external surface may exert a reaction force on the removable cap 119 in a direction that is perpendicular or otherwise non-parallel to the longitudinal axis A.

The reaction forces described above, if applied to the outer portion 166 of the removable cap 119, may cause the outer portion 166 of the removable cap 119 to bend with respect to the inner portion 168 of the removable cap 119. In at least some scenarios, the bending of the outer portion 166 of the removable cap 119 may convert kinetic energy into another form of energy such as thermal energy (e.g., heat) and/or spread out the time of an impulse. This, in turn, may reduce the likelihood of the impact event causing activation of automated or semi-automated features included in the drug delivery device including, for example, a drive mechanism for expelling a drug and/or a guard locking mechanism and/or reduce the likelihood of structural damage to components of the drug delivery device, including, for example, the removable cap 119. In at least some scenarios, the outer portion 166 of the removable cap 119 due to bending during an impact event may function as a spring-and-damper system and/or a shock absorber.

Figure 6:
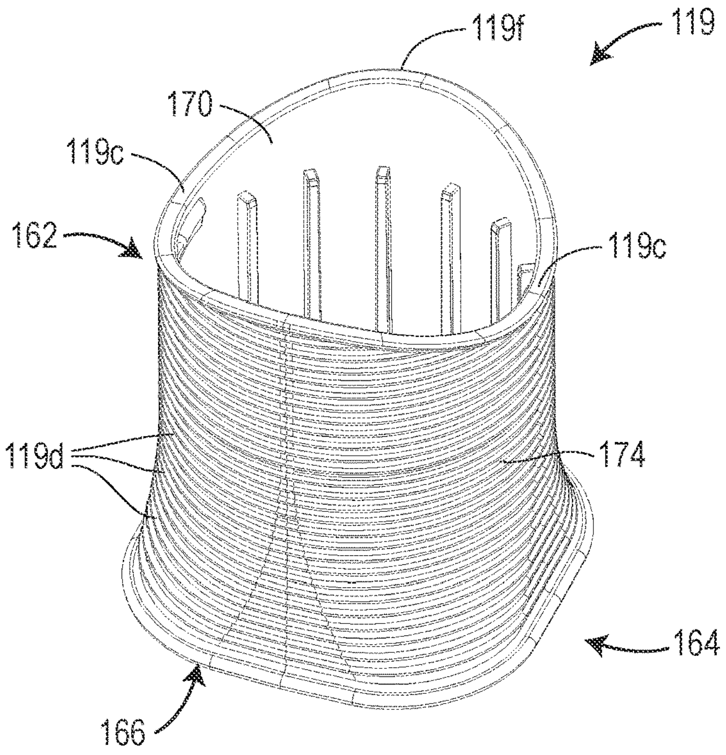
FIG. 6 is a side view of the removable cap in FIG. 4.

As seen in FIG. 6, the distal-most portion of the outer portion 166 may extend beyond the distal end of the inner portion 168 in the distal direction. In at least some scenarios, this may increase the likelihood that the outer portion 166 (not the inner portion 168) contacts the ground or other external surface in the event that the drug delivery device is dropped with the removable cap 119 facing generally downwards. In some embodiments, one or more of the corners of distal end of the outer portion 166 may define the distal-most portion of the removable cap 119, such that one or more of the corners first contacts the ground or other external surface in the event that the drug delivery device is dropped with the removable cap 119 facing generally downwards. In alternative embodiments, a distally directed end surface of the outer portion 166 may be generally level with a distally directed end surface of the inner portion 168 in a direction along the longitudinal axis A. In still further alternative embodiments, the distal-most portion of the inner portion 168 may extend beyond the distal-most portion of the outer portion 166 in the distal direction.

The removable cap 119 or at least the outer portion 166 of the removable cap 119 and/or the distal end 164 of the removable cap 119 may be made partially or entirely of a resilient (e.g., elastic) material. The resilient material may allow the removable cap 119 to deform from its original shape when subjected to an external force and upon removal of that external force regain its original shape, completely or at least partially. As an example, the entire removable cap 119 or at least the outer portion 166 of the removable cap 119 and/or at least the distal end 164 of the removable cap 119 may be made partially or entirely of a polypropylene material, a polypropylene random copolymer material, Bormed™ RF830MO, or any other suitable material. Constructing the removable cap 119 or at least the outer portion 166 of the removable cap 119 and/or at least the distal end 164 of the removable cap 119 partially or entirely from a resilient material may facilitate the above-described bending and/or shock absorbing characteristics of the removable cap 119.

Figure 9:
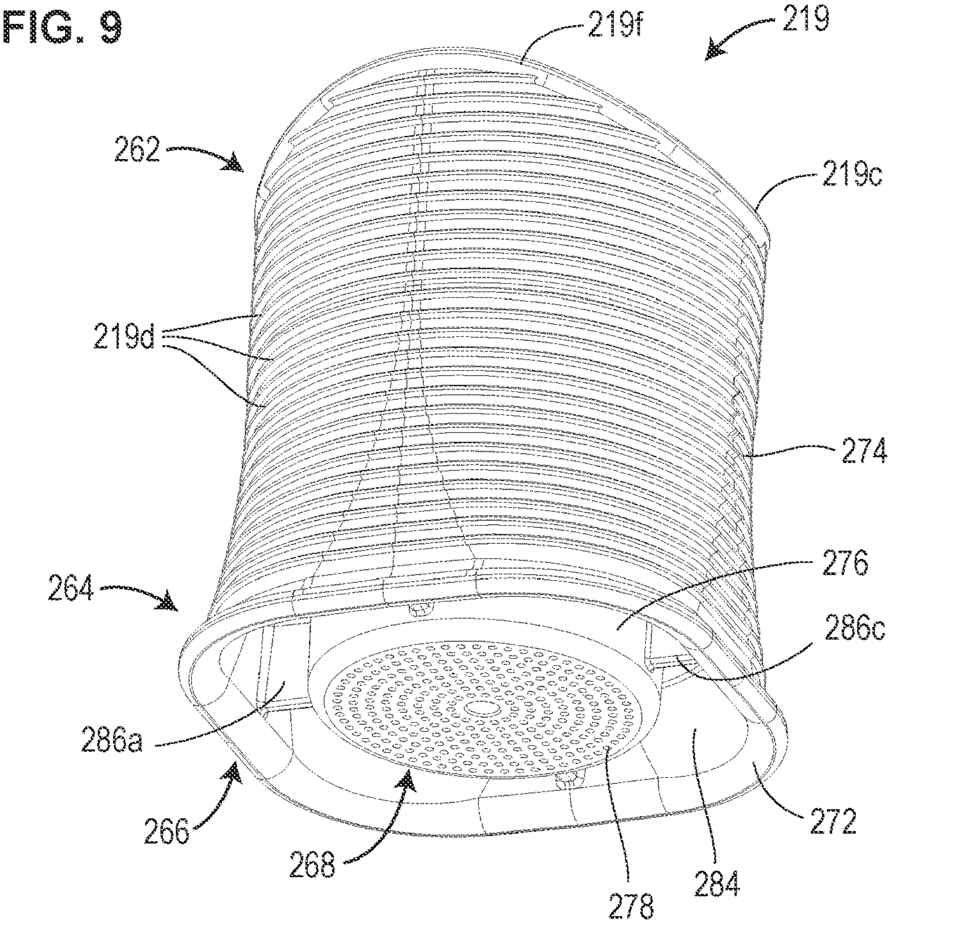
FIG. 9 is a perspective view of another exemplary removable cap in accordance with various embodiments.
Figure 10:
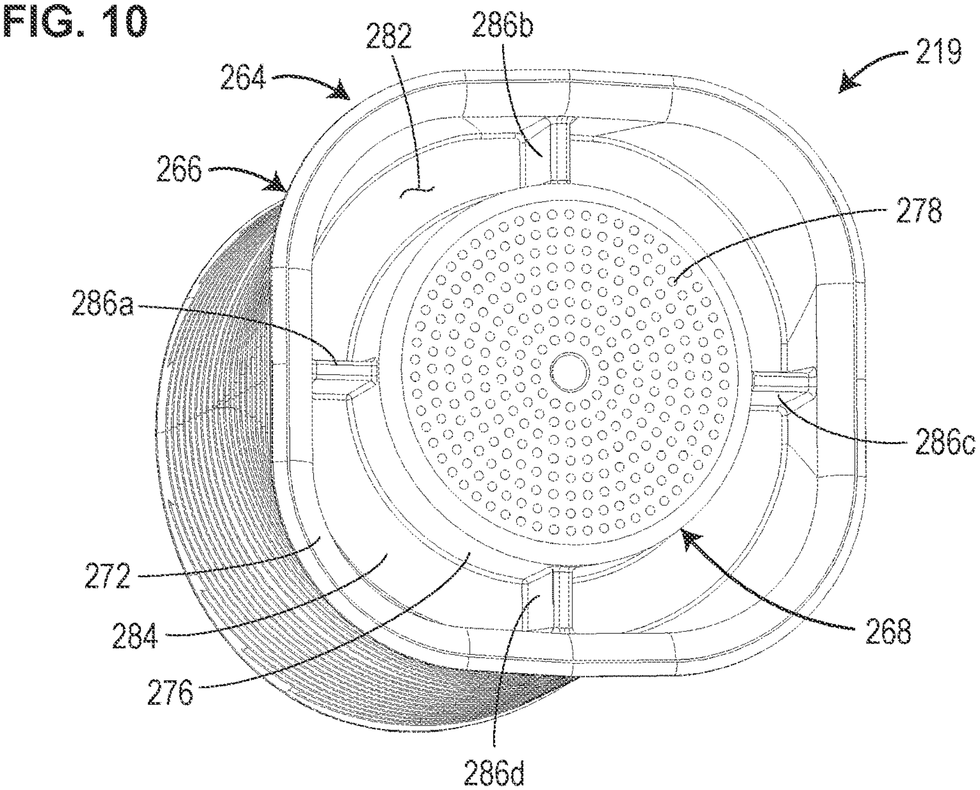
FIG. 10 is another perspective view of the distal end of the removable cap in FIG. 9.
Figure 11:
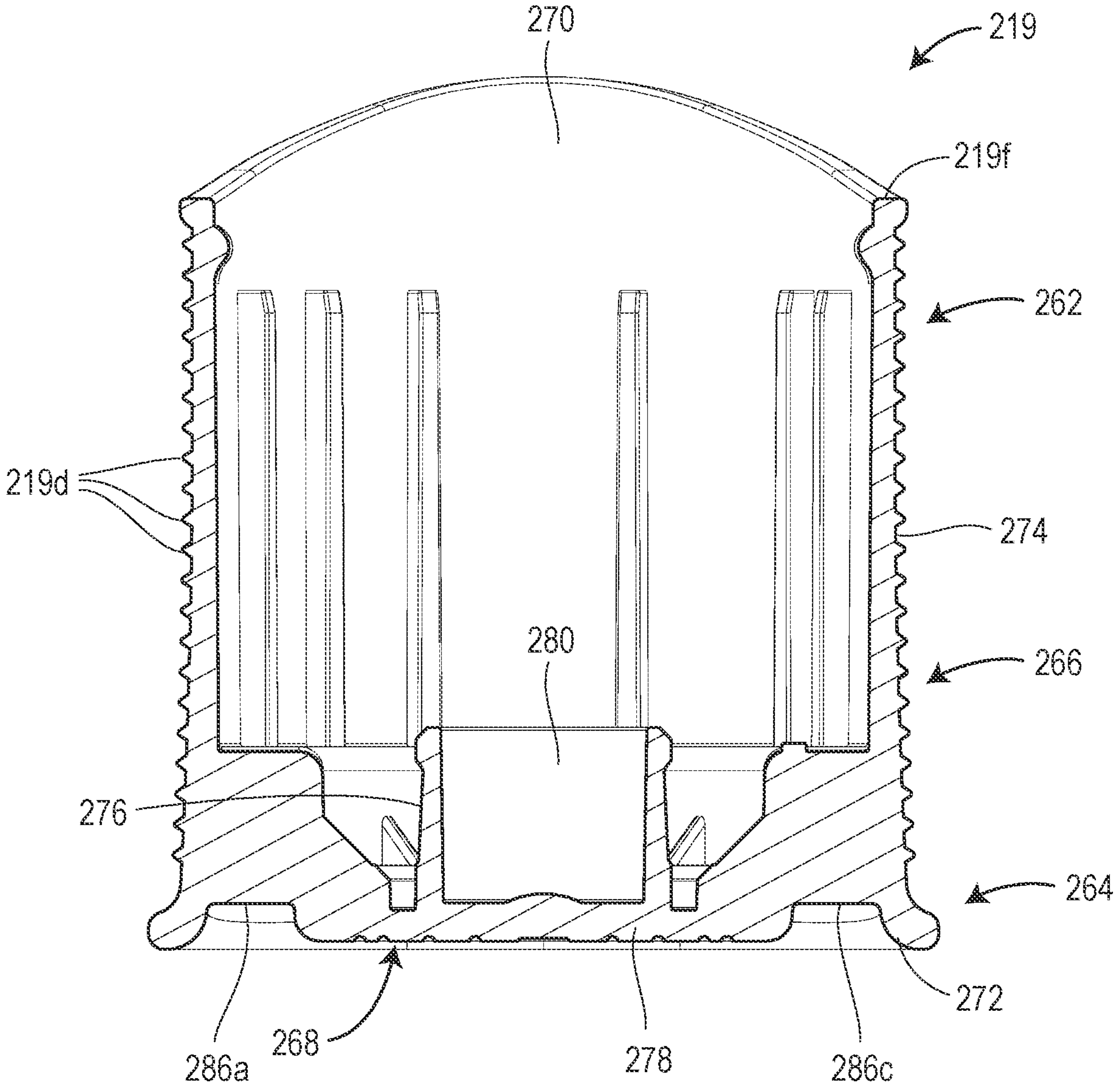
FIG. 11 is a cross-sectional view of the removable cap in FIG. 9.

Referring to FIGS. 9-11, another embodiment of a removable cap will be now described. The removable cap 219 illustrated in FIGS. 9-11 includes many similar or identical elements as those shown in FIGS. 4-8 and described above. The elements of the removable cap 219 not described in more detail below may have similar or identical structure, configuration, and/or function as the correspondingly numbered elements described above with respect to the removable cap 119 shown in FIGS. 4-8.

The removable cap 219 may include one or more support members 286*a-d* positioned radially between the outer portion 266 and the inner portion 268. Each of the support members 286*a-d* may be coupled with the outer portion 266 and/or the inner portion 268. As an example, each of the support members 286*a-d* may be coupled with the sidewall 276 of the inner portion 268, the flange 282 of the inner portion 268, and/or the wall 274 of the outer portion 266. As a more specific example, each of the support members 286*a-d* may be defined by a wall or rib extending generally in a radial direction with respect to the longitudinal axis A. Furthermore, each of the support members 286*a-d* may span an entirety of or a portion of a radial distance between the outer portion 266 and the inner portion 268. In the axial direction, the support members 286*a-d* may be arranged distal to the flange 282. In the circumferential direction, the support members 286*a-d* may be arranged at a respective circumferential positions around the sidewall 276 of the inner portion 268.

In some embodiments, the support members 286*a-d* may be configured to limit and/or control the bending of the outer portion 266 of the removable cap 219 with respect to the inner portion 268 of the removal cap 219 in the event that the outer portion 266 of the removable cap 219 is subjected to an external force, such as the reaction force applied by the ground in the drop scenario described above. By limiting and/or controlling the bending of the outer portion 266, the support members 286*a-d* may reduce the possibility of the external force causing structural damage, such as cracks or fractures, to the outer portion 266 and/or another portion of the removable cap 219.

Turning to FIGS. 12-17, additional embodiments of a removable cap will now be described. The removable caps 319, 419, and 519 illustrated in FIGS. 12-17 include many similar or identical elements as those shown in FIGS. 4-11 and described above. The elements of the removable caps 319, 419, and 519 not described in more detail below may have similar or identical structure, configuration, and/or function as the correspondingly numbered elements described above with respect to the removable caps shown in FIGS. 4-11.

Figure 12:
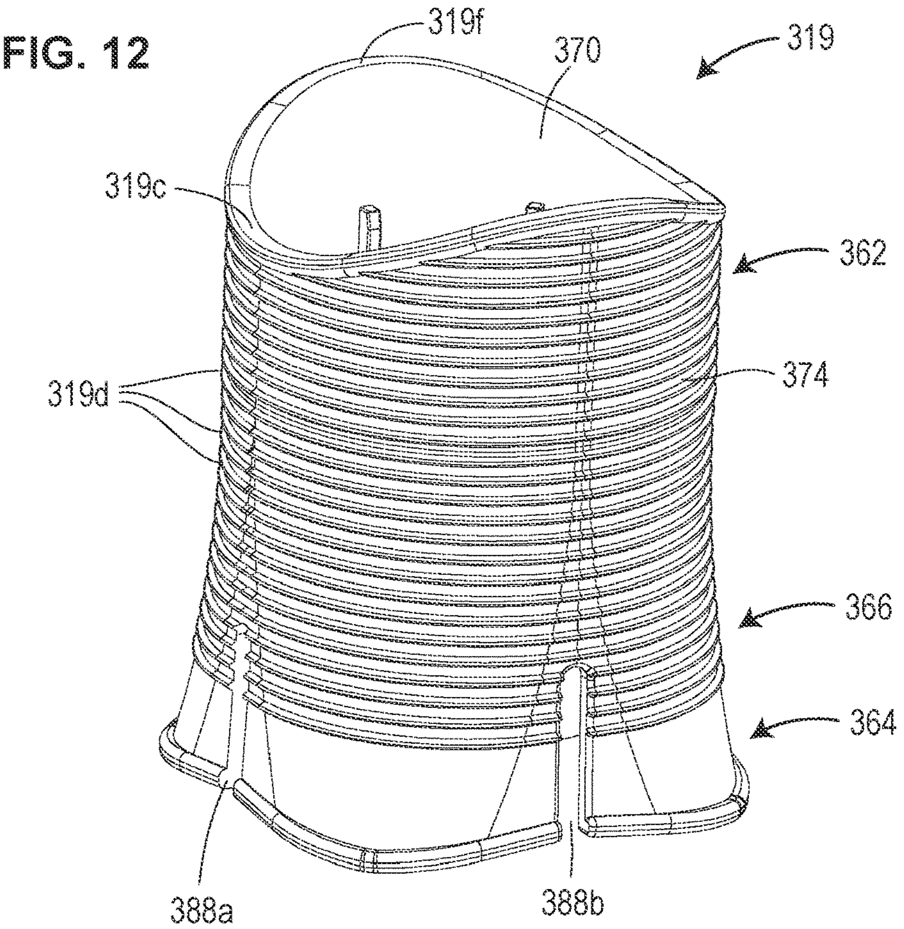
FIG. 12 is a perspective view of another exemplary removable cap in accordance with various embodiments.
Figure 13:
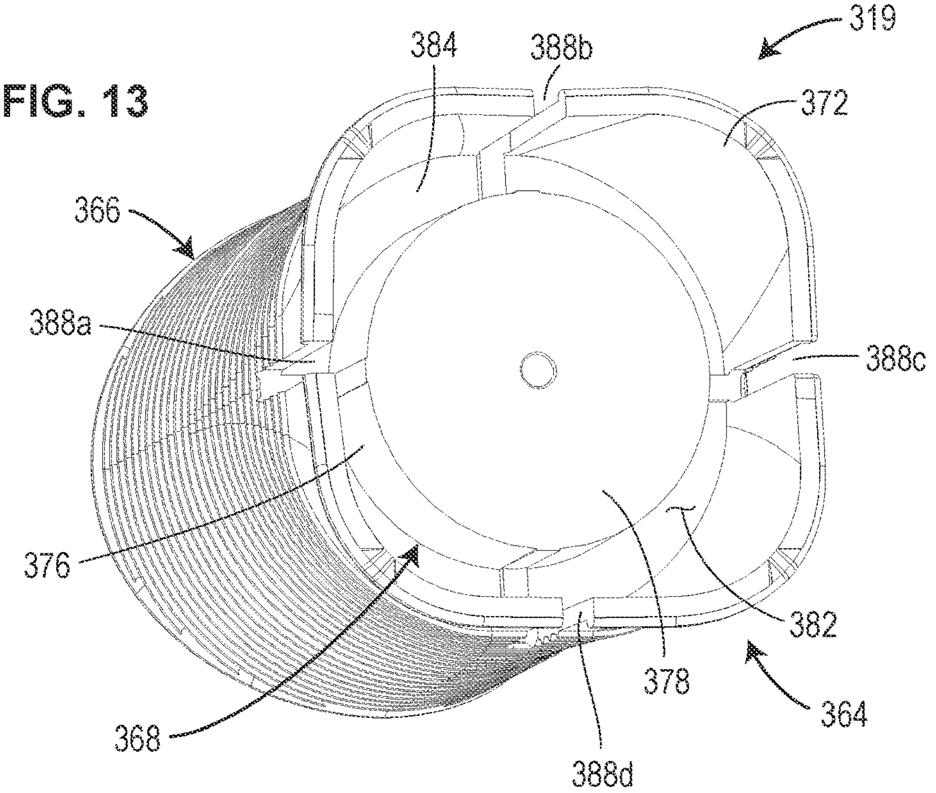
FIG. 13 is another perspective view of the distal end of the removable cap in FIG. 12.

FIGS. 12 and 13 illustrate an embodiment of a removable cap 319 including one or more side openings 388*a-d* formed in the wall 374 of the outer portion 366. Each of the side openings 388*a-d* may communicate with the gap 384. Additionally, each of the side openings 388*a-d* may communicate with the second axial opening 372 and may be formed at least partially in the distally directed end surface of the wall 374 of the outer portion 366. In the axial direction, the side openings 388*a-d* may be partially or entirely distal to the flange 382 of the inner portion 382. In the circumferential direction, the side openings 388*a-d* may be arranged at a respective circumferential positions around the wall 374 of the outer portion 366. For example, as seen in FIGS. 12 and 13, each of the side openings 388*a-d* may be located generally halfway between a respective two adjacent corners of the distal end 364 of the of the removable cap 319. Each of the side openings 388*a-d* may have a generally elongate shape such that a longest dimension or length of each of the side openings 388*a-d* is generally parallel to the longitudinal axis A. As an example, each of the side openings 388*a-d* may have an elongated oval or ellipse shape as seen in FIGS. 12 and 13. Alternatively, each of the openings 388*a-d* may have a circular, square, rectangular, or any other suitable shape.

In some embodiments, the side openings 388*a-d* may be configured to facilitate bending of the outer portion 366 of the removable cap 319 with respect to the inner portion 368 of the removal cap 319 in the event that the outer portion 366 of the removable cap 319 is subjected to an external force, such as the reaction force applied by the ground in the drop scenario described above. For example, the side openings 388*a-d* may permit portions of the outer portion 366 of the removable cap 319 to move independently of each other and/or provide additional modes of bending as compared to if the side-openings 388*a-d* were omitted. Additionally or alternatively, the side openings 388*a-d* may limit and/or focus stress concentrations to a desired or predetermined portion of the outer portion 366, for example, a portion of the outer portion 366 having a thinner and/or more compliant or flexible wall as compared to other portions of the outer portion 366.

Figure 14:
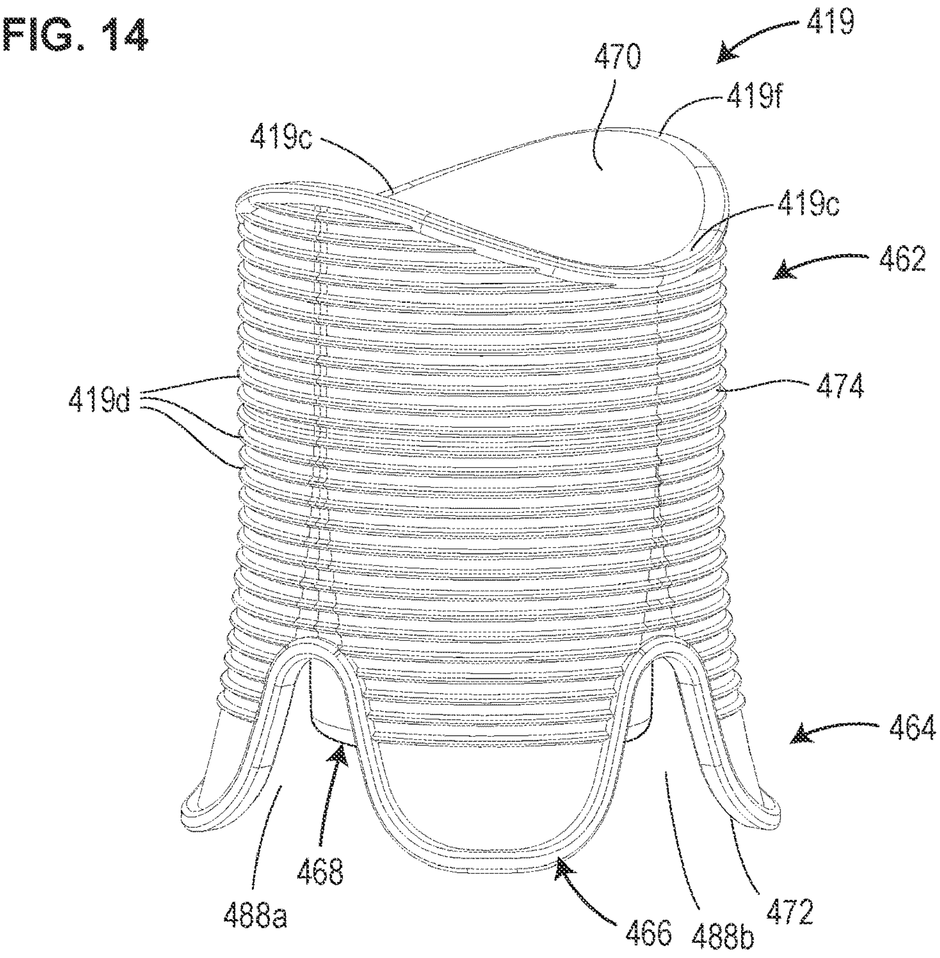
FIG. 14 is a perspective view of another exemplary removable cap in accordance with various embodiments.
Figure 15:
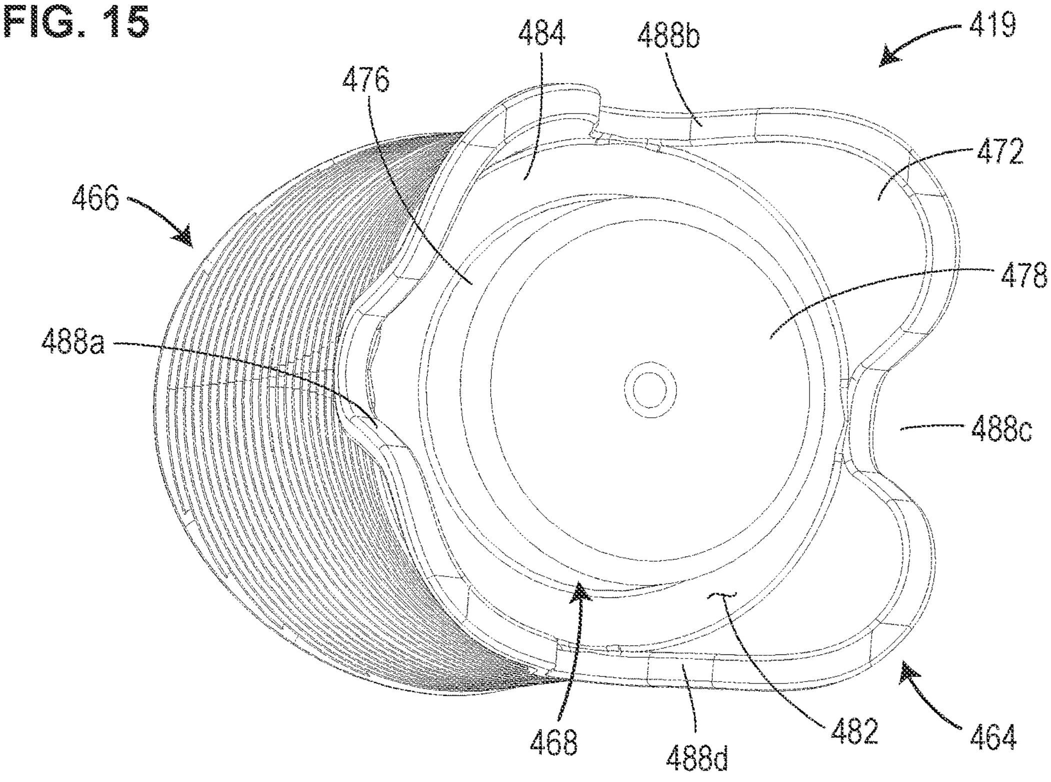
FIG. 15 is another perspective view the distal end of the removable cap in FIG. 14.

FIGS. 14 and 15 illustrate an alternative embodiment of the removable cap shown in FIGS. 12 and 13. The removable cap 419 includes side openings 488*a-d* that are similar to the side openings 388*a-d* of the removable cap 319, except for example in terms of their shape. Each of the side openings 488*a-d* has a width W that gradually decreases starting at the distally directed end surface of the wall 474 and moving in the proximal direction. As an example, each of the side openings 488*a-d* may be generally V-shaped or U-shaped when viewed from the side, as shown in FIG. 14. The shape and/or location of the openings 488*a-d* may facilitate bending of the outer portion 466 of the removable cap 419 with respect to the inner portion 468 of the removal cap 419 in the event that the outer portion 466 of the removable cap 419 is subjected to an external force, such as the reaction force applied by the ground in the drop scenario described above. For example, the side openings 488*a-d* may permit portions of the outer portion 466 of the removable cap 419 to move independently of each other and/or provide additional modes of bending as compared to if the side-openings 488*a-d* were omitted. Additionally or alternatively, the side openings 488*a-d* may limit and/or focus stress concentrations to a desired or predetermined portion of the outer portion 466, for example, a portion of the outer portion 466 having a thinner and/or more compliant or flexible wall as compared to other portions of the outer portion 466.

Figure 16:
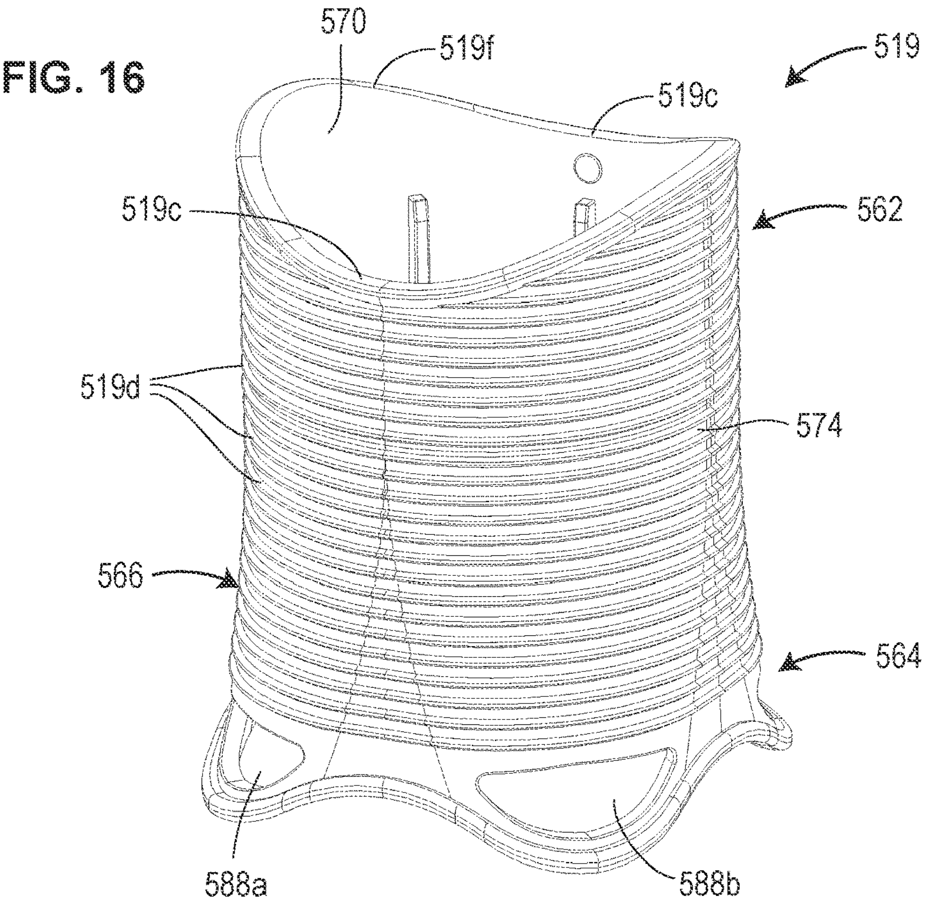
FIG. 16 is a perspective view of another exemplary removable cap in accordance with various embodiments.
Figure 17:
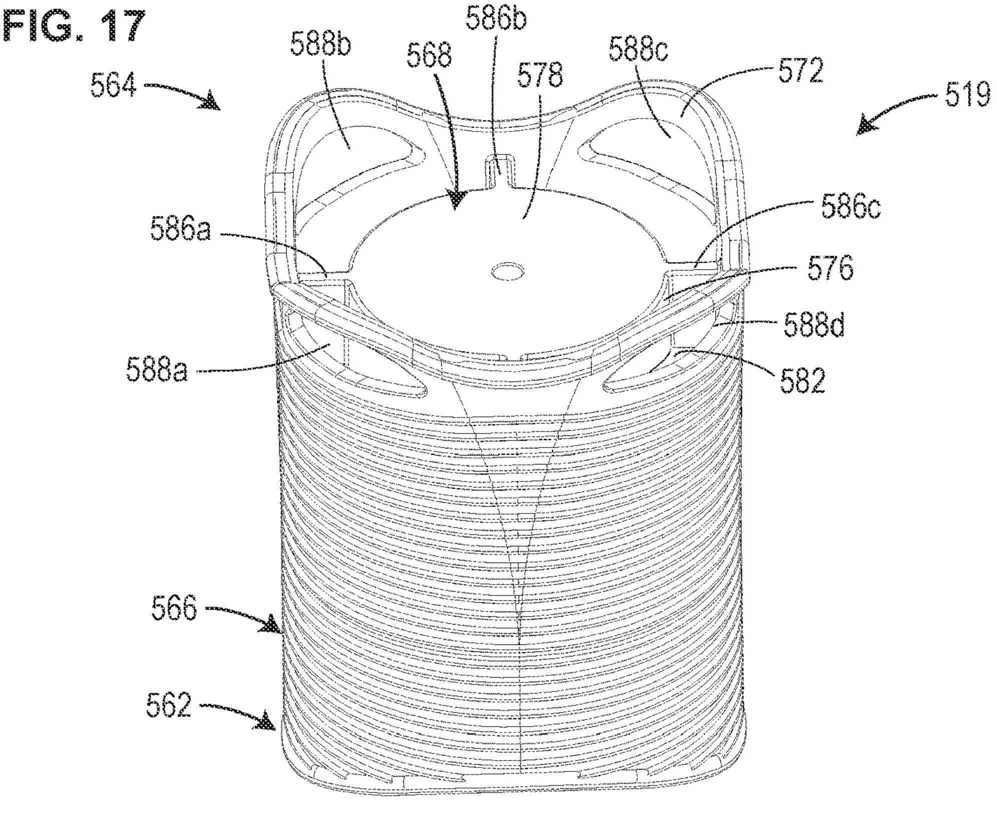
FIG. 17 is another perspective view of the distal end of the removable cap in FIG. 16.

FIGS. 16 and 17 depict another embodiment of a removable cap 519 including one or more side openings 588*a-d* formed in the wall 574 of the outer portion 566. Each of the side openings 588*a-d* may communicate with the gap 584. In the axial direction, the side openings 588*a-d* may be partially or entirely distal to the flange 582 of the inner portion 582 and/or proximal to the distally directed end surface of the wall 574 of the outer portion 566. In the circumferential direction, the side openings 588*a-d* may be arranged at a respective circumferential positions around the wall 574 of the outer portion 566. For example, as seen in FIGS. 16 and 17, each of the side openings 588*a-d* may be disposed at a respective corner of the of the distal end 564 of the of the removable cap 519. As a more specific example, each of the side openings 588*a-d* may disposed at a respective corner of the of the distal end 564 of the of the removable cap 519 such that half of each respective side opening is disposed on one side of a respective corner and the other half of the respective side opening is disposed on the other side of the respective corner. The shape and/or location of the openings 588*a-d* may facilitate bending of the outer portion 566 of the removable cap 519 with respect to the inner portion 568 of the removal cap 519 in the event that the outer portion 566 of the removable cap 519 is subjected to an external force, such as the reaction force applied by the ground in the drop scenario described above. For example, the side openings 588*a-d* may permit portions of the outer portion 566 of the removable cap 519 to move independently of each other and/or provide additional modes of bending as compared to if the side-openings 588*a-d* were omitted. Additionally or alternatively, the side openings 588*a-d* may limit and/or focus stress concentrations to a desired or predetermined portion of the outer portion 566, for example, a portion of the outer portion 566 having a thinner and/or more compliant or flexible wall as compared to other portions of the outer portion 566.

Figure 18:
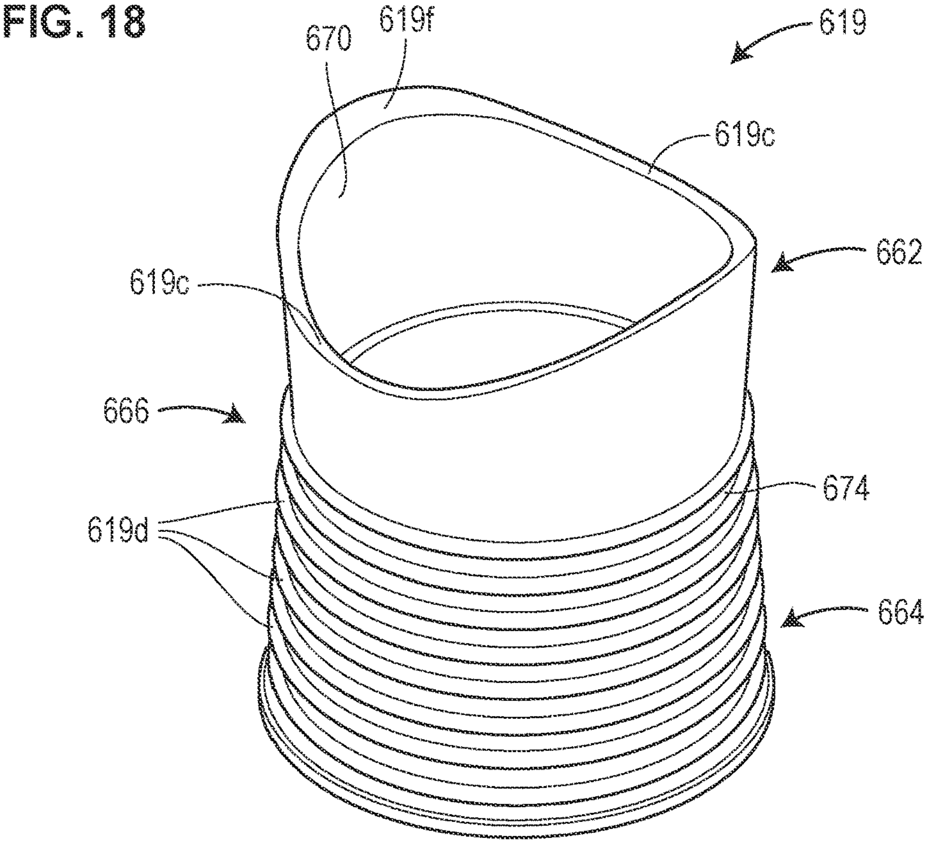
FIG. 18 is a perspective view of another exemplary removable cap in accordance with various embodiments.
Figure 19:
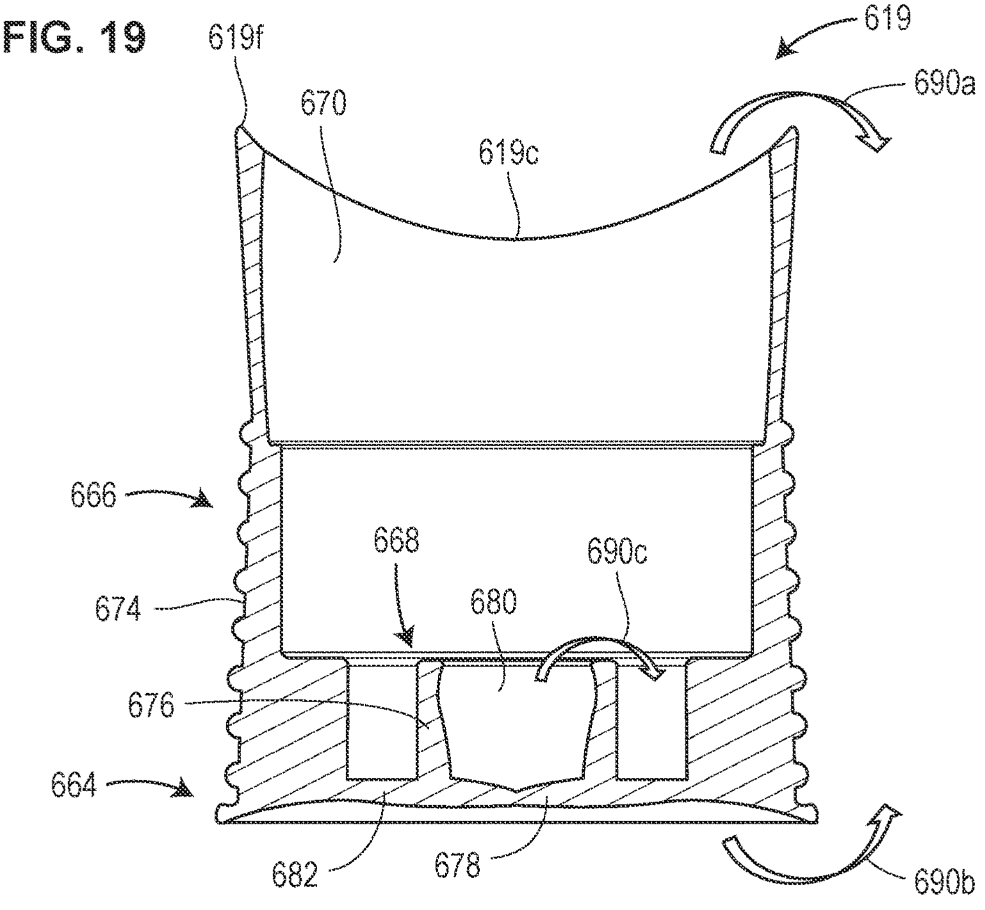
FIG. 19 is a cross-sectional view of the removable cap in FIG. 18.

Referring now to FIGS. 18 and 19, another embodiment of a removable cap is described. The removable cap 619 in FIGS. 18 and 19 includes many similar or identical elements as those shown in FIGS. 4-17 and described above. The elements of the removable cap 619 not described in more detail below may have similar or identical structure, configuration, and/or function as the correspondingly numbered elements described above with respect to the removable caps shown in FIGS. 4-17. In terms of structure, a difference between the removable cap 619 and the removable caps described in conjunction with FIGS. 4-17 is that the flange 682 of the inner portion 668 of the removable cap 619 extends radially outwardly from the distal end (as opposed to the proximal end) of the sidewall 676 of the inner removable cap 619, such that there is no second axial opening in the distal end 664 of the removable cap 619.

The removable cap 619 is configured such that an external force applied to the removable cap 619, such as the reaction force applied by the ground in the drop scenario described above, induces at least one bending moment in the removable cap 619. As an example, an external force applied to the removable cap 619 may induce one or more bending moments in any one or any combination of at least: (a) the proximal end 662 of the removable cap 619; (b) the distal end 664 of the removable cap 619; (c) the outer portion 666 of the removable cap 619; (d) the inner portion 668 of the removable cap 619; (e) the wall 674 of the outer portion 666 of the removable cap 619; (f) the sidewall 676 of the inner portion 668 of the removable cap 619; (g) the transverse wall 678 of the inner portion 668 of the removable cap 619; (h) the flange 682 of the inner portion 668 of the removable cap 619; and (i) a gripper (e.g., the gripper 13 described above) configured to remove a removable sterile barrier (e.g., the removable sterile barrier 21 described above). As a more specific example, and with reference to FIG. 19, an external force applied to the removable cap 619 may induce a first bending moment 690*a* in the proximal end 662 of the removable cap 619, a second bending moment 690*b* in the distal end 664 of the removable cap 619, and/or a third bending moment in the sidewall 676 of the inner portion 668 and/or a gripper (e.g., the gripper 13 described above) configured to remove a removable sterile barrier (e.g., the removable sterile barrier 21 described above). As an even more specific example, in a drop scenario where the drug delivery device falls with the longitudinal axis A generally parallel or otherwise non-perpendicular to the direction of gravity and with a distally directed end surface of the removable cap 619 facing generally downwards, the ground or other external surface striking the removable cap 619 may exert a reaction force on the removable cap 619 in a direction that is generally parallel or otherwise non-perpendicular to the longitudinal axis A and induce the first bending moment 690*a* in the proximal end 662 of the removable cap 619, the second bending moment 690*b* in the distal end 664 of the removable cap 619, and/or the third bending moment in the sidewall 676 of the inner portion 668 and/or a gripper (e.g., the gripper 13 described above) configured to remove a removable sterile barrier (e.g., the removable sterile barrier 21 described above). In at least some scenarios, the bending moment(s) induced in respective portions of the removable cap 619 may allow one or more of the respective portions to shock flex and/or function like a leaf spring shock absorber.

In some embodiments, the first bending moment 690*a* may be centered about or otherwise associated with a first bending axis, the second bending moment 690*b* may be centered about or otherwise associated with a second bending axis, and the third bending moment 690*a* may be centered about or otherwise associated with a third bending axis. As an example, the first bending moment 690*a* may correspond to or otherwise be associated with the proximal end 662 of the removable cap 619 bending partially or entirely around the first bending axis; the second bending moment 690*b* may correspond to or otherwise be associated with the distal end 664 of the removable cap 619 bending partially or entirely around the second bending axis; and/or the third bending moment 690*c* may correspond to or otherwise be associated with the sidewall 676 of the inner portion 668 and/or a gripper (e.g., the gripper 13 described above) bending partially or entirely around the third bending axis. As a more specific example, any one or any combination of the first bending axis, the second bending axis, and the third bending axis may be generally perpendicular or otherwise non-parallel to the longitudinal axis A and/or offset from the longitudinal axis A by a distance (e.g., a radial distance).

All features disclosed herein with respect to any of the removable cap embodiments may be combined in any combination, except combinations where at least some of such features are mutually exclusive.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing di merization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("ID-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™(eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP Ilb/Ilia receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-?4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN? mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF ? monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12C small molecule inhibitor, or another product containing a KRASG12C small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
- a housing having an opening;
- a drug storage container including a delivery member having an insertion end configured to extend at least partially through the opening during a delivery state;
- a removable cap including an outer portion and an inner portion, the outer portion being configured to be removably coupled with the housing such that the removable cap has a storage position where the removable cap is coupled with the housing and at least partially covering the opening and a removed position where the removable cap is not coupled with the housing; and
- wherein a gap separates at least a portion of the inner portion and at least a portion of the outer portion such that the at least a portion of the outer portion is configured to bend radially inwardly, radially outwardly, in a proximal direction, and/or in a distal direction with respect to the at least a portion of the inner portion when the at least a portion of the outer portion is subjected to an external force.

2. The drug delivery of claim 1, wherein the outer portion at least partially surrounds the inner portion.

3. The drug delivery device of claim 1, wherein the removable cap has a first axial opening configured to receive the housing and a second axial opening.

4. The drug delivery device of claim 3, wherein the outer portion at least partially surrounds the first axial opening and the second axial opening.

5. The drug delivery device of claim 1, wherein the gap is a radial gap.

6. The drug delivery device of claim 1, wherein the removable cap comprises at least one support member disposed between the inner portion and the outer portion, the at least one support member being coupled with at least one of the inner portion and the outer portion.

7. The drug delivery device of claim 6, wherein the at least one support member is coupled with the inner portion and the outer portion.

8. The drug delivery device of claim 6, wherein the at least one support member comprises a plurality of support members arranged at a respective circumferential positions around the inner portion.

9. The drug delivery device of claim 1, comprising at least one side opening formed in the outer portion and communicating with the gap.

10. The drug delivery device of claim 9, wherein the at least one side opening is at least partially formed in a distally directed end surface of the outer portion.

11. The drug delivery device of claim 9, wherein the at least one side opening is proximal to a distally directed end surface of the outer portion.

12. The drug delivery device of claim 9, wherein the at least one side opening comprises a plurality of side openings arranged at respective circumferential positions around the outer portion.

13. The drug delivery device of claim 1, wherein the external force is applied to the removable cap in a direction that is generally parallel to a longitudinal axis of the removable cap and/or housing and/or the removable cap is configured such that the external force induces at least one bending moment in at least one of a proximal end of the removable cap and a distal end of the removable cap.

14. A drug delivery device comprising:
- a housing having an opening;
- a drug storage container including a delivery member having an insertion end configured to extend at least partially through the opening during a delivery state;
- a removable cap including a proximal end and a distal end, the proximal end being configured to be removably coupled with the housing such that the removable cap has a storage position where the removable cap is coupled with the housing and at least partially covering the opening and a removed position where the removable cap is not coupled with the housing; and
- wherein the removable cap is configured such that an external force applied to the removable cap induces at least one bending moment in at least one of the proximal end of the removable cap and the distal end of the removable cap.

15. The drug delivery device of claim 14, wherein the at least one bending moment comprises a first bending moment in the proximal end of the removable cap and a second bending moment in the distal end of the removable cap.

16. The drug delivery device of claim 14, wherein the at least one bending moment is associated with at least a portion of the proximal end of the removable cap bending at least partially around a first bending axis.

17. The drug delivery device of claim 16, wherein the at least a portion of the proximal end of the removable cap comprises an annular wall.

18. The drug delivery device of claim 16, wherein the at least one bending moment is associated with at least a portion of the distal end of the removable cap bending at least partially around a second bending axis.

19. The drug delivery device of claim 14, wherein the external force is applied to the removable cap in a direction that is generally parallel to a longitudinal axis of the removable cap and/or housing.

20. The drug delivery device of claim 14, wherein the removable cap comprises an outer portion and an inner portion, and wherein a gap separates at least a portion of the inner portion and at least a portion of the outer portion such that the at least a portion of the outer portion is allowed to bend with respect to the at least a portion of the inner portion if the at least a portion of the outer portion is subjected to the external force.

* * * * *